United States Patent [19]
Mine et al.

[11] Patent Number: 5,810,009
[45] Date of Patent: Sep. 22, 1998

[54] ULTRASONIC PROBE, ULTRASONIC PROBE DEVICE HAVING THE ULTRASONIC PROBE, AND METHOD OF MANUFACTURING THE ULTRASONIC PROBE

[75] Inventors: Yoshitaka Mine, Nishinasuno-Machi; Haruyasu Rokurouta, Otawara, both of Japan

[73] Assignee: Kabushiki Kaisha Toshiba, Kawasaki, Japan

[21] Appl. No.: 534,201

[22] Filed: Sep. 26, 1995

[30] Foreign Application Priority Data

Sep. 27, 1994 [JP] Japan .................................... 6-231590
Apr. 28, 1995 [JP] Japan .................................... 7-106670

[51] Int. Cl.$^6$ .................................................... A61B 8/00
[52] U.S. Cl. ..................................... 128/662.03; 310/334
[58] Field of Search ........................ 128/662.03, 662.06; 29/25.35; 310/334

[56] References Cited

U.S. PATENT DOCUMENTS 4,862,893  9/1989  Martinelli ........................... 128/662.03
5,295,487  3/1994  Saitoh et al. ........................ 128/662.03

*Primary Examiner*—Francis Jaworski
*Attorney, Agent, or Firm*—Oblon, Spivak, McClelland, Maier & Neustadt, P.C.

[57] ABSTRACT

In an ultrasonic prove, a plurality of ultrasonic transducer elements are set in array. Each of the plurality of ultrasonic transducer elements has an outer surface consisting of a front surface for transmitting and receiving an ultrasonic signal, a back surface opposite to the front surface, and a side surface connecting between the front surface and the back surface. Each of the plurality of ultrasonic transducer elements is driven by a driving electric signal so as to transmit and receive the ultrasonic signal. The ultrasonic prove is comprised of a pair of electrodes covered with at least a portion of at least the front surface of each of the plurality of ultrasonic transducer elements and the side surface thereof and a pair of conductors joined to the pair of electrode of each of the transducer elements respectively. The joined positions of the pair of conductors are positioned on at least one of sides of the front surface of each of the transducer elements and side surface thereof.

23 Claims, 27 Drawing Sheets

ULTRASONIC PROBE, ULTRASONIC PROBE DEVICE HAVING THE ULTRASONIC PROBE, AND METHOD OF MANUFACTURING THE ULTRASONIC PROBE

BACKGROUND OF THE INVENTION

1. Field of the Invention

The present invention relates to an ultrasonic probe for use in, for example, an ultrasonic diagnosis apparatus, an ultrasonic probe device having such an ultrasonic probe, and a method of manufacturing the ultrasonic probe. More particularly, the present invention relates to an ultrasonic probe characterized in the connection structure of an ultrasonic transducer and in the transducer element division and interconnection processes.

2. Description of the Related Art

Ultrasonic diagnosis apparatus are ones which diagnose an organism on the basis of an ultrasonic signal reflected from the organism and have been applied in various medical fields in recent years. Concretely, ultrasonic diagnosis apparatus are designed to scan an organism with an ultrasonic signal using an ultrasonic probe device and to produce ultrasonic images of an organism, speed data on a kinetic fluid in an organism and so on, on the basis of an echo signal from the organism.

Ultrasonic probe devices are classified into various types by scanning means and scanning type. Ultrasonic probe devices are classified by scanning means into mechanical scanning type probe device in which an ultrasonic probe device is itself mechanically moved for scanning at a high speed, and electronic scanning type probe devices in which a phased array type ultrasonic transducer, which is an array of a large number of fine transducer elements, is moved for scanning under an electronic control (this type of ultrasonic probe device is called a phased array type ultrasonic probe device). Ultrasonic probe devices are also classified by scanning type into sector scanning type probe devices, linear scanning type probe devices, convex scanning type probe devices and radial scanning type probe devices. These various types of probe devices are chosen in use to suit a desired objective of diagnosis or the portion of a body of a subject.

FIGS. 43 and 44 illustrates a probe head structure of a conventional phased array, linear scanning type (or sector scanning type) ultrasonic probe device from which an acoustic lens is removed.

A probe head of an ultrasonic probe device 201 has an ultrasonic transducer 202. A rubber backing member 203 is adhered to the back surface of the ultrasonic transducer 202. An acoustic lens (not shown) is provided on the ultrasonic wave radiating surface (front surface) of the ultrasonic transducer 202 through a plurality of acoustic matching layers 204 and 205.

A flexible printed circuit (hereinafter referred to as an FPC) 206 and a grounding plate 207 made of copper are joined to the back surface of the ultrasonic transducer 202 from two sides thereof by, for example, soldering as if they protrude from the ultrasonic transducer 202.

The ultrasonic transducer 202 is made of a flat plate-like ceramic piezoelectric member with a signal electrode 208 and a grounding electrode 209 formed on two surfaces thereof. The signal electrode 208 is formed on the back surface of the ultrasonic transducer 202. The grounding electrode 209 is formed on the front surface thereof. The grounding electrode 209 formed on the front surface of the ultrasonic transducer 202 extends through one side surface thereof to the portion of the back surface thereof. The portion of the grounding electrode 209 formed on the signal electrode side is electrically connected to a grounding plate 207 on the back surface of the ultrasonic transducer 202. The signal electrode 208 is electrically connected to a conductive pattern of the FPC 206.

When the ultrasonic probe device 201 is to be manufactured, the signal electrode 208 and the grounding electrode 209 are formed on a flat plate-like ceramic piezoelectric member to constitute the ultrasonic transducer 202. The FPC 206 is connected to one end portion of the back surface of the ultrasonic transducer 202, while the grounding plate 207 is joined to the other end portion of the back surface thereof by, for example, soldering. The plurality of acoustic matching layers 204 and 205 and the backing member 203 are respectively adhered to the front and back surfaces of the ultrasonic transducer 202 with the FPC 206 and the grounding plate 207 joined thereto.

Thereafter, the ultrasonic transducer 202 is cut into transducer elements 202a using a dies to obtain an array of transducer elements 202a. A silicon adhesive is filled in a gap between the adjacent transducer elements 202a. Finally, an acoustic lens (not shown) is provided on the acoustic matching layers 204 and 205 of the ultrasonic transducer 202, whereby an ultrasonic probe is constructed. This ultrasonic probe is incorporated in a probe head to manufacture an ultrasonic probe device.

To manufacture a convex scanning type ultrasonic probe device, a flat plate-like ceramic piezoelectric member to which a flexible backing member adhires is used for an ultrasonic transducer 202'. The ultrasonic transducer 202' is cut into transducer elements 202a' to constitute an array of transducer elements 202a', as in the case of the phased array, linear scanning type ultrasonic probe device. After the cutting which provides its entire flexibility, the entire ultrasonic transducer is curved along a direction in which the transducer elements are arrayed until a desired curvature is obtained, and then adhered to a container having a curved surface of the same curvature as that of the ultrasonic transducer. Thereafter, the ultrasonic transducer is subjected to the gap filling process and the acoustic lens providing process to construct a convex scanning type ultrasonic probe. This ultrasonic probe is incorporated in a probe head, whereby an ultrasonic probe device is manufactured.

A radial scanning type probe is manufactured in the same manner as that of the convex scanning type probe with the exception that a cylindrical container is used and that the entire ultrasonic transducer is adhered annularly on the outer peripheral surface of that container.

As mentioned above, in the conventional ultrasonic probe device 201, the FPC 206 and the grounding plate 207 are joined to one end portion of the back surface of the ultrasonic transducer 202 and the other end portion thereof by, for instance, soldering in such a manner that they protrude therefrom. Thereafter, the transducer 202 with the FPC 206 and the grounding plate 207 joined thereto is cut according to the conductive pattern of the FPC 206 using a dies to divide the transducer into the transducer elements 202a.

However, in the above ultrasonic probe device, since the FPC 206 and the grounding plate 207 protrude curvedly from the ultrasonic transducer 202, it is difficult to provide a compact ultrasonic prove device .

Further, in the conventional ultrasonic probe device, after the FPC 206 and the grounding plate 207 have been joined to the transducer 202, that transducer 202 is cut at a pitch of the conductive pattern of the FPC 206. However, it is very difficult to cut the ultrasonic transducer 202 in the pitch of the conductive pattern of the FPC 206, deteriorating yield. Further, in the manufactured ultrasonic transducer 202, it is difficult to obtain transducer elements having a pitch of, for instance, 0.15 mm or below because there are restrictions on the conductive pattern pitch of the FPC 206 and because the transducer element pitch is restricted by that conductive pattern pitch.

Since the FPC 206 and the grounding plate 207 are joined to the back surface of the ultrasonic transducer 202 by, for example, soldering, the electrode extending portions (about 2 mm) of the FPC 206 and grounding plate 207 affect the effective aperture L of the ultrasonic transducer 202. In an ultrasonic probe device, such as an endoscopic probe device, in which the width of the transducer 202 in a sliced direction is, for example, about 10 mm, the effective aperture will be reduced to about 5 to 6 mm, thus reducing resolution.

After the FPC 206 and the grounding plate 207 have been joined to the ultrasonic transducer 202 by, for example, soldering, that ultrasonic transducer 202 is cut into the plurality of transducer elements 202a. Thus, electrode peel-off may occur during division of the transducer and/or it is difficult to set the cutting dies accurately at an initial position in the conductive pattern of the FPC 206.

Furthermore, since the FPC 206 and the grounding plate 207 are adhered to the back surface of the ultrasonic transducer 202, the back surface thereof cannot be entirely covered with the backing member 203. Accordingly, adhesion between the transducer 202 and the backing member 203 is weakened, and consequently, yield is reduced.

Particularly, in a convex scanning type (or radial type) ultrasonic probe device, since the FPC and the grounding plate are joined to the transducer before the transducer is curved, softness of the transducer is reduced by the hardness of the FPC and grounding plate. When the transducer is curved in that state after being cut, the pitch of the transducer elements may be deflected because of shortage of softness. This is the reason why it is difficult to manufacture convex scanning type and radial scanning type ultrasonic probe devices having a curvature radius of 10 mm or below. Particularly, it is impposible to manufacture electronic radial scanning type ultrasonic probe device for use in a body cavity because it requires a smaller curvature than that of the convex scanning type and radial scanning type ultrasonic probe devices.

In a conventional ultrasonic probe device, although the transducer elements are connected to a power source via an interconnection material, such as the conductive pattern of the FPC, desired signal line connection is connection of an interconnection material, such as coaxial cables or wires, to the electrode layer of the transducer element.

However, in the above-described ultrasonic probe device manufacturing method, signal line connection is performed before division of the transducer. Since division of the transducer is very difficult after signal line connection has been performed by using an interconnection material, such as wires. Thus, signal line connection using an interconnection material, such as wires, without using an FPC, cannot be performed in the above-described ultrasonic probe device manufacturing method.

SUMMARY OF THE INVENTION

The present invention is directed to overcoming the aforementioned problem. That is, an object of the present invention is to provide an ultrasonic probe in which connection of signal lines or grounding electrodes is performed on a surface of an ultrasonic transducer other than a back surface (for instance, a side surface) thereof to improve manufacturing property and hence productivity of the probe, thus increasing yield, a method of manufacturing such a probe, and an ultrasonic probe device having such a probe.

Another object of the present invention is to provide an ultrasonic probe which does not require a cutting position adjusting operation of setting a transducer element pitch of an ultrasonic transducer with a pattern on a flexible printed circuit, which can eliminate the restrictions on the transducer element pitch of the ultrasonic transducer by the pattern of the flexible printed circuit, and which can improve productivity, a method of manufacturing such an ultrasonic probe, and an ultrasonic probe device incorporating such an ultrasonic probe.

Still another object of the present invention is to provide an ultrasonic probe in which signal lines or grounding electrode connection is performed on the side surface of an ultrasonic transducer so that electrode extending portions do not reduce a probe effective opening and the probe effective opening can thus be increased, a method of manufacturing such an ultrasonic probe, and an ultrasonic probe device incorporating such an ultrasonic probe.

Still another object of the present invention is to provide an ultrasonic probe which enables miniaturization of transducer elements of an ultrasonic transducer, a method of manufacturing such an ultrasonic probe, and an ultrasonic probe device incorporating such an ultrasonic probe, particularly, a method of manufacturing small-sized radial scanning type and convex scanning type ultrasonic probes which enable a plurality of transducer elements to be arrayed on a curved or cylindrical surface having a fine curvature.

Still another object of the present invention is to provide an ultrasonic probe which enables cutting of an ultrasonic transducer to be continuously performed so as to improve productivity, a method of manufacturing such an ultrasonic probe, and an ultrasonic probe device incorporating such an ultrasonic probe.

In order to achieve the above-described objects, according a first aspect of the present invention, there is provided an ultrasonic probe, in which an ultrasonic transducer has an outer surface consisting of a front surface for transmitting and receiving an ultrasonic signal, a back surface opposite to the front surface, and a side surface connecting between the front surface and the back surface and the ultrasonic transducer is driven by a driving electric signal so as to transmit and receive the ultrasonic signal, the ultrasonic probe comprising a pair of electrodes covered with at least a portion of at least the front surface of the ultrasonic transducer and the side surface thereof and a pair of conductors joined to the pair of electrode respectively, said jointed positions of the pair of conductors being positioned on at least one of sides of the front surface of the ultrasonic transducer and side surface thereof.

In preferred embodiments of this aspect, the ultrasonic transducer is divided into a plurality of ultrasonic transducer elements set in array and each of the plurality of ultrasonic transducer elements has the pair of electrodes and the pair of conductors joined to the pair of electrodes respectively. This aspect of the present invention has an arrangement that the pair of conductors include a signal conductor for transmitting and receiving the electric signal and a ground conductor for grounding and the signal conductor is a flexible printed circuit having an exposed pattern of one end and the ground conductor is a grounding plate. This aspect of the present invention has an arrangement that the joined positions of the exposed pattern of the flexible printed circuit are positioned on the one side surfaces of each of the plurality of ultrasonic transducer elements and said joined positions of the grounding plate are positioned on the other side surfaces of each of the plurality of ultrasonic transducer elements. The exposed pattern of the flexible printed circuit is joined to the electrodes of the one side surfaces of each of the plurality of ultrasonic transducer elements by soldering and said grounding plate is joined to the electrodes of the other side surfaces of each of the plurality of ultrasonic transducer elements by soldering or a conductive adhesive.

According to a second aspect of the present invention, there is provided an ultrasonic probe, in which a plurality of ultrasonic transducer elements is set in array, each of said plurality of ultrasonic transducer elements having an outer surface consisting of a front surface for transmitting and receiving an ultrasonic signal, a back surface opposite to the front surface, and a side surface connecting between the front surface and the back surface, and each of the plurality of ultrasonic transducer elements is driven by a driving electric signal so as to transmit and receive the ultrasonic signal, the prove comprising an acoustic matching layer formed on a front surface of each of the plurality of ultrasonic transducer elements, a backing member provided on the back side of each of the plurality of ultrasonic transducer elements, an acoustic lens provided in such a manner that the lens covers the acoustic matching layer, a pair of electrodes covered with at least a portion of at least the front surface of each of the plurality of ultrasonic transducer elements and the side surface thereof, and a pair of conductors joined to the pair of electrode of each of the plurality of ultrasonic transducer elements, respectively, said jointed positions of the pair of conductors being positioned on at least one of sides of the front surface of each of the plurality of ultrasonic transducer elements and side surface thereof. In a preferred embodiment of this this aspect, the backing member includes a first backing member joined to the transducer elements and having a thickness of not more than 5 mm and a second backing member joined to the first backing member.

According to a third aspect of the present invention, there is provided an ultrasonic probe, in which an electric signal is transmitted to a plurality of ultrasonic transducer elements set in array, each of said plurality of ultrasonic transducer elements having an outer surface consisting of a front surface for transmitting and receiving an ultrasonic signal, a back surface opposite to the front surface, and a side surface connecting between the front surface and the back surface, and each of the plurality of ultrasonic transducer elements is driven by the electric signal so as to transmit and receive the ultrasonic signal, the prove comprising an acoustic matching layer on a front surface of each of the plurality of ultrasonic transducer elements, a pair of electrodes covered with at least a portion of at least the back surface and the side surface of each of the plurality of ultrasonic transducer elements, a backing member having a surface on which a conductive pattern formed in a predetermined pitch and signal line connecting portions electrically connected to the conductive pattern are formed, said surface of the backing material being electrically adhered with the back surface of each of the plurality of ultrasonic transducer elements, a signal conductor joined to each of the signal line connecting portions, a grounding plate joined to the electrode covered with one of the side surfaces of each of the plurality of ultrasonic transducer elements, and an acoustic lens provided in such a manner that the lens covers the acoustic matching layer.

According to a fourth aspect of the present invention, there is provided a method of manufacturing an ultrasonic probe comprising the steps of constructing an ultrasonic transducer by forming a pair of electrodes on a surface of a ceramic piezoelectric member, joining an acoustic matching layer on a front surface of the ultrasonic transducer from which an ultrasonic signal is transmitted and received and a backing member on a back surface opposite to the front surface of the ultrasonic transducer, cutting the ultrasonic transducer with the acoustic matching layer and backing member joined thereto along a certain direction at a predetermined pith so as to divide a plurality of ultrasonic transducer elements set in array, and joining a pair of conductors to the pair of electrodes of each of the plurality of ultrasonic transducer elements for transmitting an electrical signal to each of the plurality of ultrasonic transducer elements so as to drive each of the plurality of ultrasonic transducer elements and to transmit and receive the ultrasonic signal.

In preferred embodiments of this aspect, the one of the pair of conductors is a flexible printed circuit having an exposed pattern of one end and the other is a grounding plate. This aspect of the present invention has an arrangement that joining of the flexible printed circuit and the grounding plate is performed by joining the exposed pattern of the flexible printed circuit to the electrodes on one side surfaces of each of the transducer elements by soldering while joining a grounding plate to the electrodes on the other side surfaces of each of the transducer elements by soldering or using a conductive adhesive.

According to a fifth aspect of the present invention, there is provided a method of manufacturing an ultrasonic probe comprising the steps of preparing both an ultrasonic transducer with a pair of electrodes formed on at least a back surface opposite to a front surface of the ultrasonic transducer from which an ultrasonic signal is transmitted and received and a backing member having a surface on which a conductive pattern formed in a predetermined pitch and signal line connecting portions electrically connected to the conductive pattern are formed, electrically adhering the back surface of the ultrasonic transducer with the conductive pattern formed surface of the backing member, cutting the ultrasonic transducer electrically adhered to the backing member according to the conductive pattern at a predetermined pith so as to divide a plurality of ultrasonic transducer elements set in array, joining one of a pair of conductors to the signal line connecting portions of the backing member and the other to the electrode of each of the ultrasonic transducer elements for transmitting an electrical signal to each of the plurality of ultrasonic transducer elements so as to drive each of the plurality of ultrasonic transducer elements and to transmit and receive the ultrasonic signal.

According to a sixth aspect of the present invention, there is provided a method of manufacturing an ultrasonic probe comprising the steps of constructing an ultrasonic transducer by forming a pair of electrodes on a surface of a ceramic piezoelectric member, joining an acoustic matching layer on a front surface of the ultrasonic transducer from which an ultrasonic signal is transmitted and received and a backing member on a back surface opposite to the front surface of the ultrasonic transducer, cutting the ultrasonic transducer with the backing member joined thereto along a certain direction at a predetermined pith so as to divide a plurality of ultrasonic transducer elements set in array, joining a pair of conductors to the pair of electrodes of each of the plurality of ultrasonic transducer elements for transmitting an electrical signal to each of the plurality of ultrasonic transducer elements so as to drive each of the plurality of ultrasonic transducer elements and to transmit and receive the ultrasonic signal, and curving the ultrasonic transducer and the backing material along the array direction so as to make the front surface curved.

In preferred embodiments of this aspect, the one of the pair of conductors is a flexible printed circuit having an exposed pattern of one end and the other is a grounding plate. This aspect of the present invention has an arrangement that joining of the flexible printed circuit and the grounding plate is performed by joining the exposed pattern of the flexible printed circuit to the electrodes on one side surfaces of each of the transducer elements by soldering while joining a grounding plate to the electrodes on the other side surfaces of each of the transducer elements by soldering or using a conductive adhesive.

According to a seventh aspect of the present invention, there is provided a method of manufacturing an ultrasonic probe comprising the steps of constructing an ultrasonic transducer by forming a pair of electrodes on a surface of a ceramic piezoelectric member, joining an acoustic matching layer on a front surface of the ultrasonic transducer from which an ultrasonic signal is transmitted and received and a backing member on a back surface opposite to the front surface of the ultrasonic transducer, cutting the ultrasonic transducer with the backing member joined thereto along a certain direction at a predetermined pith so as to divide a plurality of ultrasonic transducer elements set in array, curving the ultrasonic transducer and the backing material along the array direction so as to make the front surface curved, and joining a pair of conductors to the pair of electrodes of each of the plurality of ultrasonic transducer elements for transmitting an electrical signal to each of the plurality of ultrasonic transducer elements so as to drive each of the plurality of ultrasonic transducer elements and to transmit and receive the ultrasonic signal.

According to an eighth aspect of the present invention, there is provided a method of manufacturing an ultrasonic probe comprising the steps of preparing both an ultrasonic transducer with a pair of electrodes formed on at least a back surface opposite to a front surface of the ultrasonic transducer from which an ultrasonic signal is transmitted and received and a backing member having a surface on which a conductive pattern formed in a predetermined pitch and signal line connecting portions electrically connected to the conductive pattern are formed, electrically adhering the back surface of the ultrasonic transducer with the conductive pattern formed surface of the backing member, cutting the ultrasonic transducer electrically adhered to the backing member according to the conductive pattern at a predetermined pith so as to divide a plurality of ultrasonic transducer elements set in array, joining one of a pair of conductors to the signal line connecting portions of the backing member and the other to the electrode of each of the ultrasonic transducer elements for transmitting an electrical signal to each of the plurality of ultrasonic transducer elements so as to drive each of the plurality of ultrasonic transducer elements and to transmit and receive the ultrasonic signal, and curving the ultrasonic transducer and the backing material along the array direction so as to make the front surface curved.

According to a ninth aspect of the present invention, there is provided an ultrasonic probe device having an ultrasonic prove incorporated in a prove head of the ultrasonic probe device, in which an electric signal is transmitted to a plurality of ultrasonic transducer elements set in array, each of said plurality of ultrasonic transducer elements having an outer surface consisting of a front surface for transmitting and receiving an ultrasonic signal, a back surface opposite to the front surface, and a side surface connecting between the front surface and the back surface, and each of the plurality of ultrasonic transducer elements is driven by the electric signal so as to transmit and receive the ultrasonic signal, the prove device comprising an acoustic matching layer formed on a front surface of each of the plurality of ultrasonic transducer elements, a backing member provided on the back side of each of the plurality of ultrasonic transducer elements, an acoustic lens provided in such a manner that the lens covers the acoustic matching layer, a pair of electrodes covered with at least a portion of at least the front surface and the side surface of each of the plurality of ultrasonic transducer elements, a pair of conductors joined to the pair of electrode of each of the plurality of ultrasonic transducer elements, respectively, said jointed positions of the pair of conductors being positioned on at least one of sides of the front surface and side surface of each of the plurality of ultrasonic transducer elements.

In the ultrasonic probe according to the present invention, a pair of electrodes is covered at least a portion of at least the front surface and the side surface. A pair of conductors (which may be a flexible printed circuit having an exposed pattern of one end and a grounding plate) is joined to the pair of electrode respectively. The jointed positions of the pair of conductors are positioned on at least one of sides of the front surface and side surface. Thus, since the jointed position of the flexible printed circuit is positioned on at least one of sides of the front surface and side surface not the back surface, the flexible printed circuit does not protrude from the sides of the transducer elements. Therefore, a small and compact ultrasonic probe can be gotten. Furthermore, since the flexible printed circuit does not cover the electrode forming surfaces of the transducer elements from above or below, the jointed positions of the pair of conductors do not affect the electrode effective aperture, thus enabling the electrode effective aperture to be effectively increased.

The exposed pattern of the flexible printed circuit is joined to the one side surfaces of the transducer elements by soldering, while the grounding plate is joined to the other side surfaces of the transducer elements by soldering or using a conductive adhesive. Thus, the flexible printed circuit and the grounding plate do not protrude from the sides of the transducer elements. Therefore, a small and compact ultrasonic probe can be provided. In addition, a large electrode effective aperture of the ultrasonic transducer can be gotten.

Where the grounding prate is joined to the other side surfaces of the transducer elements by soldering or using a conductive adhesive, joining of the grounding plate can be performed after division of the ultrasonic transducer into the transducer elements. Thus, a problem involving electrode peel-off, which would occur during division of the ultrasonic transducer, can be eliminated, and connection can be performed smoothly and readily.

Where the exposed pattern of the flexible printed circuit is joined to the one side surfaces of the ultrasonic transducers by soldering, joining of the flexible printed circuit can be performed after division of the ultrasonic transducer into the transducer elements. Thus, a problem involving electrode peel-off, which would occur during division of the ultrasonic transducer, can be eliminated, and connection can be performed smoothly and readily.

Particularly, since the thickness of the backing member has a thickness of not more than 5 mm, cooling property of the backing member is improved. Accordingly, adverse effect of thermal expansion of the backing member on the accuracy with which the transducer is formed can be lessened, and consequently, the transducer element pitch forming accuracy can be improved.

In the ultrasonic probe manufacturing method according to the present invention, since the ultrasonic transducer is divided into the transducer elements and then the conductor, such as a flexible printed circuit, is joined to the electrode jointing portions of those transducer elements, division of the ultrasonic transducer into transducer elements can be performed in a state where no conductor is joined thereto. Further, division of the ultrasonic transducer can be performed regardless of the pitch of the conductive pattern of the conductor, such as a flexible printed circuit. Thus, yield of the products can be improved, thus improving productivity.

Furthermore, since the conductor is joined to the ultrasonic transducer after the division of the ultrasonic transducer into the transducer elements, deterioration in the yield, which would conventionally occur during soldering required for joining the conductor or during division of the ultrasonic transducer, can be eliminated.

Further, since the exposed pattern of the flexible printed circuit is joined by soldering to the one side surfaces of the transducer elements of the ultrasonic transducer while the grounding plate is joined to the other side surfaces of the transducer elements by soldering or using a conductive adhesive, reduction in the effective aperture for ultrasonic waves by the electrode extending portions can be reliably lessened. Thus, the effective aperture for ultrasonic waves can be made larger than that of a conventional foot print.

Further, since the conductor joining position to the transducer element is the portion of the electrode layer of the transducer element located on the front or side surface thereof, the back surface of the transducer element can be joined directly to the backing member. Thus, joining between the transducer plate and the backing member can be intensified, and yield can thus be increased.

In the ultrasonic probe according to the present invention, the conductive pattern having a predetermined pitch and the signal line connecting portions including the conductive pattern are formed on the front surface of the backing member, and the conductor is joined to the signal line connecting portions for extending the signal lines. Thus, connection of the signal lines is further facilitated.

In the ultrasonic probe manufacturing method according to the present invention, after the ultrasonic transducer with the pair of electrodes formed thereon has been divided into the transducer elements set in array, the pair of conductors are joined to the pair of electrodes. Next, the ultrasonic transducer having the transducer elements is curved along the array direction so as to make the front surface curved. That is, since no conductor, such as a flexible printed circuit or a grounding plate, is joined to the ultrasonic transducer at that time of division thereof, deficiency caused by the hardness of the flexible printed circuit or the grounding plate during division can be alleviated, enabling convex type and radial type ultrasonic probe having a fine curvature to be readily manufactured.

In the ultrasonic probe manufacturing method according to the present invention, the conductive pattern having a predetermined pitch and the signal line connecting portions including the conductive pattern are formed on the front surface of the backing member, and the flexible printed circuit, which is the conductor for transmitting and receiving the electric signal, is joined to the signal line connecting portions. Thus, connection of the conductor for transmitting and receiving the electric signal is further facilitated.

In the ultrasonic probe device according to the present invention, at least one of the electrode plates of the ultrasonic probe is constituted by a flexible printed circuit, and the exposed pattern thereof is joined to one side surface of the transducer element group of the ultrasonic transducer. Thus, the flexible printed circuit does not protrude from the side of the transducer element group, thus enabling provision of a small and compact ultrasonic probe device.

Further, since the flexible printed circuit is joined to one side surface of the ultrasonic transducer and thus does not cover the electrode forming surface from above or below, the probe effective aperture of the ultrasonic probe device can be made large. Thus, the effective aperture for ultrasonic waves can be made larger than that of a conventional foot print.

Other objects and advantages of the invention will be apparent from the following description taken in connection with the accompanying drawings.

DETAILED DESCRIPTION OF THE PREFERRED EMBODIMENTS

Embodiments of the present invention will now be described with reference to the accompanying drawings.

Figure 1:
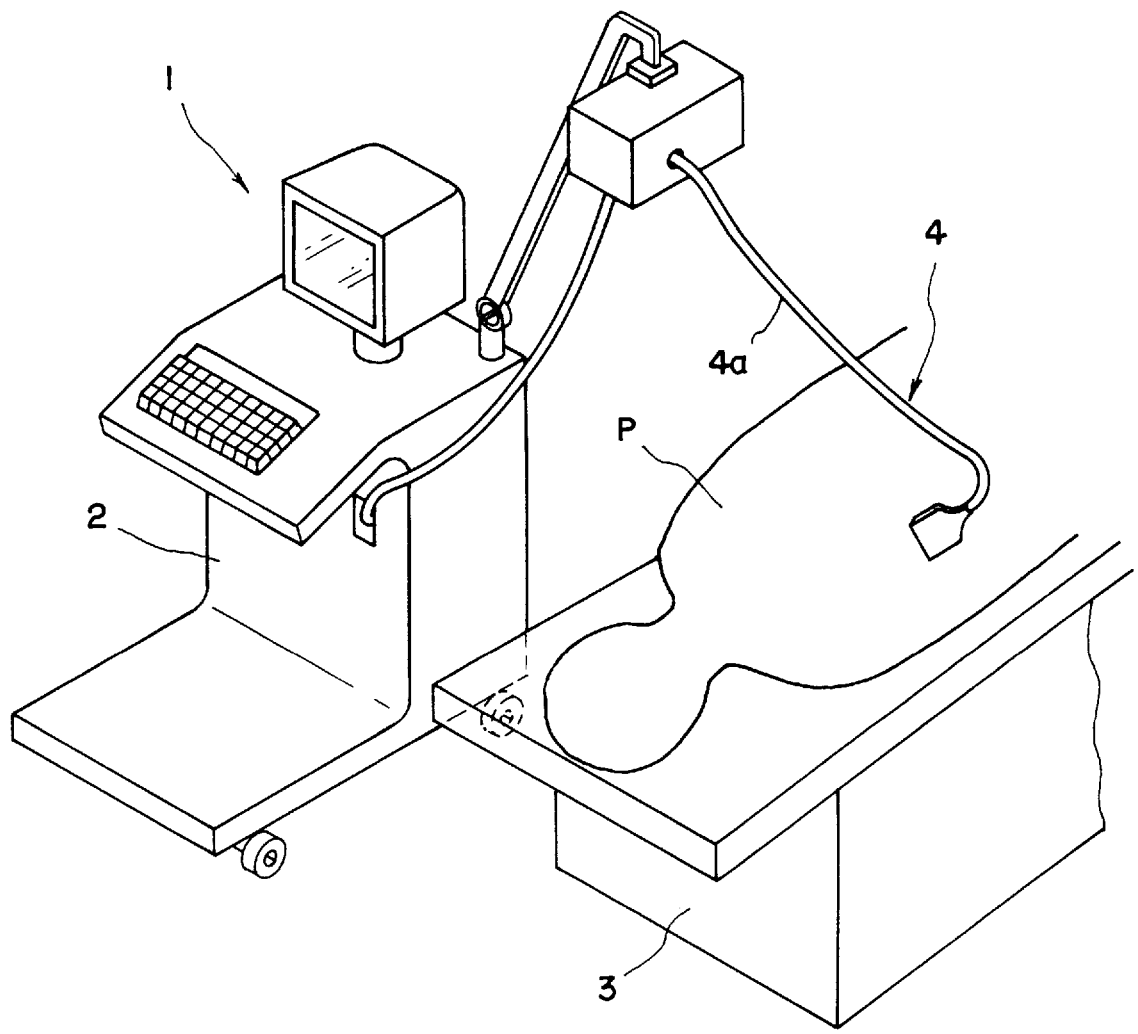
FIG. 1 is a schematic perspective view of an ultrasonic prove device in a first embodiment according to the present invention.

FIG. 1 is a schematic perspective view illustrating a ultrasonic diagnosis apparatus 1 having a console 2 for controlling the ultrasonic diagnosis apparatus 1 wholly, a bed 3 on which a patient P lies as a subject being diagnosed, and an ultrasonic prove device 4 for transmitting an ultrasonic signal to the patient P and for receiving an ultrasonic signal (echo signal) therefrom.

Figure 2:
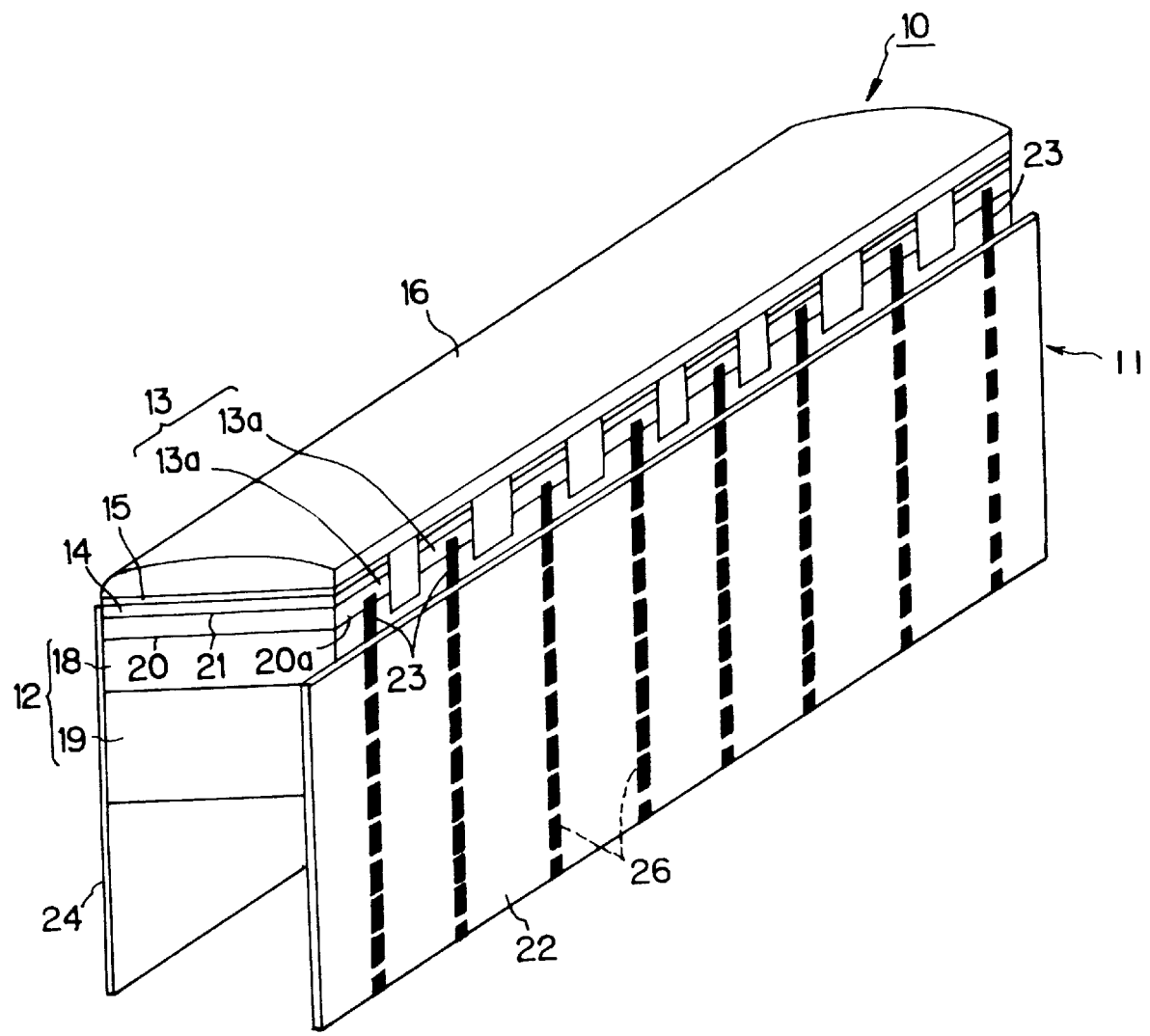
FIG. 2 is a greatly enlarged schematic perspective view of an ultrasonic probe to be provided in a probe head of the ultrasonic probe device shown in FIG. 1.

FIG. 2 is a schematic perspective view illustrating a probe head 10 of the ultrasonic probe device 4 shown in FIG. 1 according to a first embodiment of the present invention in an enlarged fashion. The ultrasonic probe device shown in FIG. 2 is a linear scanning type probe device. The present invention can also be applied to a phased array, sector scanning type probe device. Ultrasonic probe devices of the type in which an ultrasonic wave radiating surface is curved, such as convex scanning type ultrasonic probe devices or radial scanning type ultrasonic probe devices, will be described later.

The probe head 10 of the ultrasonic probe device has an ultrasonic probe 11, as shown in FIG. 2. The ultrasonic probe 11 has a rectangular ultrasonic transducer 13 with acoustic matching layers 14 and 15 provided on a front surface of the ultrasonic transducer 13 from which the ultrasonic signal is transmitted so as to allow the ultrasonic signal to be readily transmitted and received into an organism of the patient P. The backing member 12 is provided on a back surface opposite to the front surface thereof. An acoustic lens 16 is provided on an upper surface of the acoustic matching layer 15. The backing member 12 and the acoustic matching layers 14 and 15 are respectively joined to the back and front surfaces of the ultrasonic transducer 13 using a heat reaction type film-shaped adhesive. Remaining surfaces except the front surface and back surface correspond to side surfaces.

The heat reaction type film-shaped adhesive is an adhesive whose main component is, for example, an epoxy modified resin. When this film-shaped adhesive is used to join the backing member 12 and the acoustic matching layers 14 and 15, soiling of the side surface of the ultrasonic transducer 13, which would occur when an adhesive is used, can be avoided.

The backing member 12 has a multi-layer, e.g., double-layer, structure. The backing member 12 is divided into a first backing member 18 constituting a first backing layer which is thin and placed on top of the other layer, and a second backing material 19 constituting a second backing layer which is a reinforcing lower layer.

The first backing member 18 is made of a soft material having a large coefficient of thermal expansion, such as rubber, in a plate-like shape. The first backing member 18 has a thickness of 5 mm or below. The second backing member 19 forms a reinforcing layer, and is made of a hard material having a small coefficient of thermal expansion, for example, a glass or bakelite plate. In other words, a soft material having a coefficient of linear expansion equal to or greater than a predetermined coefficient of linear expansion (which may be $40 \times 10^{-6}$) to form the first backing member 18, and a hard material having a coefficient of linear expansion smaller than the predetermined coefficient of linear expansion is used to form the second backing member 19.

The second backing member may be replaced with a backing layer holder which is similar thereto. The backing layer holder is also made of a hard material having a small coefficient of thermal expansion (which is a hard material having a coefficient of linear expansion smaller than the predetermined coefficient of linear expansion), such as a glass or bakelite plate. The backing member 12 is joined and held on that backing layer holder.

The ultrasonic transducer 13 is constituted as a group of ultrasonic transducer elements 13a which are arrayed along a longitudinal dirrection of the ultrasonic transducer 13 on a plane and in a row. The longitudinal dirrection corresponds to an array dirrection. The transducer elements 13a are formed by finely dividing a plate-shaped ceramic piezoelectric member made of, for example, lead titanate zirconate porcelain.

Figure 3:
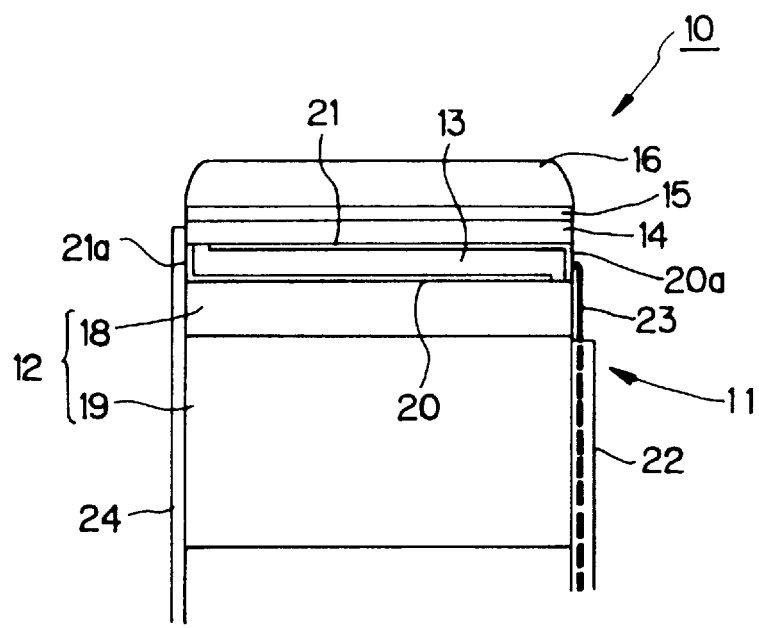
FIG. 3 is a side elevational view of the ultrasonic probe incorporated in the ultrasonic probe device shown in FIG. 2.

As shown in FIG. 3, a signal electrode 20 is formed on a back surface of each of the transducer elements 13a of the ultrasonic transducer 13. A grounding electrode 21 is formed on outer front surfaces of each of the transducer elements of the ultrasonic transducer 13 which opposes the back surface. The signal electrode 20 extends to one of the side surfaces of the transducer elements 13a of the ultrasonic transducer 13, said one of the side surfaces being along the array direction. An electrode extending portion 20a which is the signal electrode 20 formed on one of the side surfaces of the transducer elements 13a of the ultrasonic transducer 13 is then connected to an external circuit therefrom. A conductor pattern (exposed pattern) 23 having a predetermined pitch is exposed from a distal end of a flexible printed circuit 22 (hereinafter referred to as FPC) serving as an electrode plate. The conductor pattern 23 is connected to electrode extending portions 20a of the signal electrodes 20 of the transducer elements 13a by soldering. Thus, the signal electrodes 20 are extended and connected to an external circuit through the FPC 22. Soldering is performed by conducting plating on the exposed pattern 23 of the FPC 22 to a thickness of 3 to 20 $\mu$m. The non-exposed other end of the conductor pattern 23 is connected to, for example, a transmitting/receiving circuit via a connector which is not shown and a cable 4a shown in FIG. 1.

The grounding electrode 21 extends to the side surface of each of the transducer elements 13a of the ultrasonic transducer 13 which opposes the signal electrode extended side surface. An electrode extending portion 21a which is the grounding electrode 21 formed on the side surface of each of the transducer elements 13a of the ultrasonic transducer 13 is then connected to an external circuit therefrom. A copper grounding plate 24, serving as an electrode plate, is connected directly to electrode extending portions 21a of the grounding electrodes 21 by soldering. This soldering is also performed by conducting plating on the portion of the grounding plate 24 connected to the ultrasonic transducer 13 to a thickness of 3 to 20 $\mu$m. Since the FPC 22 and the grounding plate 24 are joined and connected to the side surfaces of the ultrasonic transducer 13 by soldering, the joined FPC 22 and grounding plate 24 do not protrude outwardly from the ultrasonic transducer 13, enabling a small and compact ultrasonic probe 11, constituting the probe head 20, to be provided.

The FPC 22 joined to the electrode extending portions 20a of each of the transducer elements 13a of the ultrasonic transducer 13 has a structure shown in FIG. 3 in which signal electrode lines 26, constituting the conductor pattern, are gripped and sealed by a base 27 and a cover lay 28. A distal end of the signal electrode lines 26 in the FPC 22 forms the exposed pattern 23. This exposed pattern 23 is joined to the electrode extending portions 20a of each of the transducer elements 13a of the ultrasonic transducer 13.

Figures 4A, 4B:
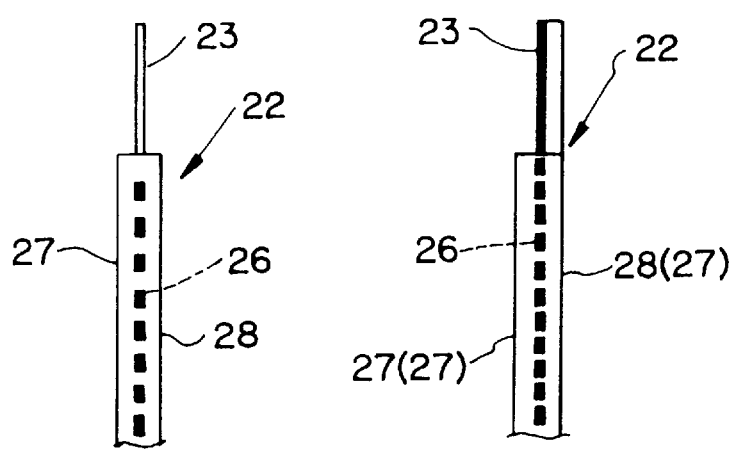
FIGS. 4(A) and 4(B) respectively illustrate a flexible printed circuit joined to an ultrasonic transducer of the ultrasonic probe.

The portion of the conductor pattern which forms the exposed pattern 23 may be completely exposed, as shown in FIG. 4(A). Alternatively, one side of that portion may be covered by the base 27 or the cover lay 28 with the other side exposed, as shown in FIG. 4(B).

Figure 5A:
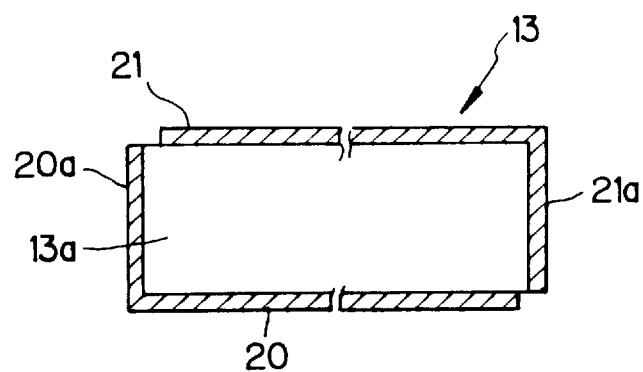
FIGS. 5(A), 5(B) and 5(C) are respectively side elevational views of ultrasonic transducers in which electrodes are formed on a ceramic piezoelectric member.
Figure 5B:
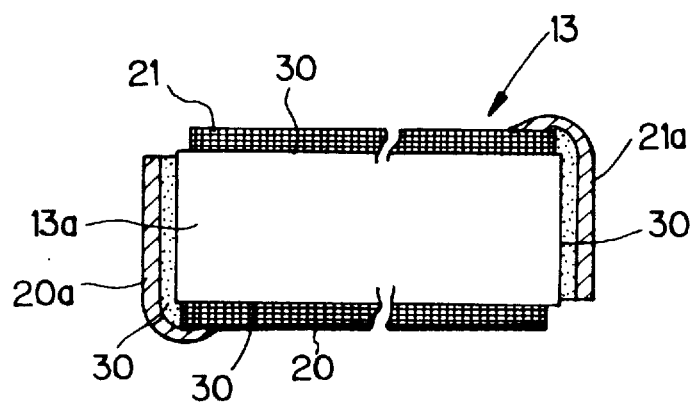
Figure 5C:
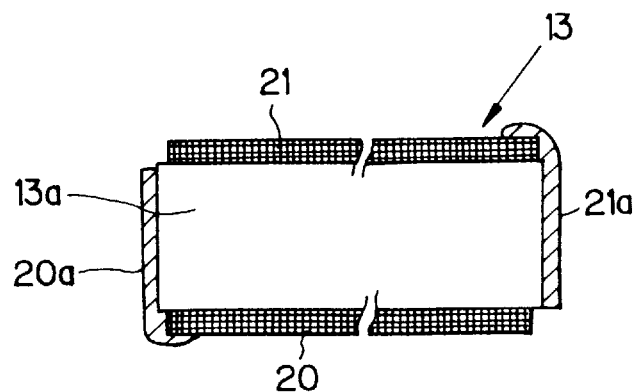

As shown in FIGS. 5(A), 5(B) or 5(C), the signal electrode 20 is formed on the back surface of each of the transducer elements 13a of the ultrasonic transducer 13. The signal electrode formed on the back surface of each of the transducer elements 13a extends to one lateral side surface thereof. The grounding electrode 21 is formed on the front surface of each of the transducer elements 13a of the ultrasonic transducer 13. The grounding electrode 21 formed on the front surface of each of the transducer elements 13a extends to the other lateral side surface thereof. The signal electrode 20 is not joined to the grounding electrode 21.

The electrodes 20 and 21 formed on the surface of each of the transducer elements of the ultrasonic transducer 13 are Au or Ag electrodes. Au or Ag electrodes may be formed by depositing, sputtering, baking or plating an Au or Ag electrode material on the surface of the ultrasonic transducer 13. Among these electrodes, Ag baked electrodes shown in FIG. 5(A) are inexpensive and easy to form.

In order to improve and increase the joining strength between the electrodes 20 and 21 and the ultrasonic transducer 13, an interposing layer 30 in which at least one element selected from a group consisting of Ni, Ti, Cr and Sn is present may be formed on the surface of the transducer element as a bonding layer, as shown in FIG. 5(B). Thereafter, Au or Ag electrodes are formed on the interposing layer 30. At that time, Ag electrodes may be formed on the interposing layers 30 formed on the side surfaces of the ultrasonic transducer 13 as the electrode extending portions 20a and 21a. The presence of the interposing layers 30 improves wattability and drape between the ultrasonic transducer 13 and the electrodes 20 and 21, and thus improves bonding strength therebetween.

Alternatively, Ag electrodes may be formed on the front and back surfaces of the ultrasonic transducer 13, while Au or Ag electrodes are formed on the side surfaces of the transducer as the electrode extending portions 20a and 21a, as shown in FIG. 5(C).

Other combinations of materials cam also be used to form the signal electrodes 20 and 21 formed on the ultrasonic transducer 13. For example, conductive materials, such as Cu or alloy materials, may be used as the electrode materials.

For diagnosis, the probe head 10 of the ultrasonic probe device 4 is brought into contact with the patient P. The transducer element 13a is driven by an electric signal controlled by the transmitting/receiving circuit to output an ultrasonic signal from the front surface thereof. The ultrasonic signal (echo signal) reflected from the organs in a body cavity of the patient P is received by the transducer elements 13a of the ultrasonic probe device. The received echo signal is sent to a DSC which is not shown via the transmitting/receiving circuit. The echo signal is converted into an image signal. The image signal is sent to a monitor which is not shown and displayed by the monitor as an ultrasonic image.

The method of manufacturing the above-described ultrasonic probe device will now be described.

FIGS. 6 through 10 respectively illustrate the manufacturing processes of the ultrasonic probe devices. To manufacture an ultrasonic probe device, a rectangular plate-shaped ceramic piezoelectric member 13A made of a ceramic material, such as lead titanate zirconate porcelain, is prepared first. As shown in FIGS. 5(A), 5(B) or 5(C), the signal electrode (Au or Ag electrode) 20 is formed on the back surface of the piezoelectric member 13A and on one longitudinal side surface thereof, and the grounding electrode (Au or Ag electrode) 21 is formed on the front surface of the ultrasonic transducer from which an ultrasonic signal is transmitted and on the other longitudinal side surface thereof to constitute the ultrasonic transducer 13.

Figure 6:
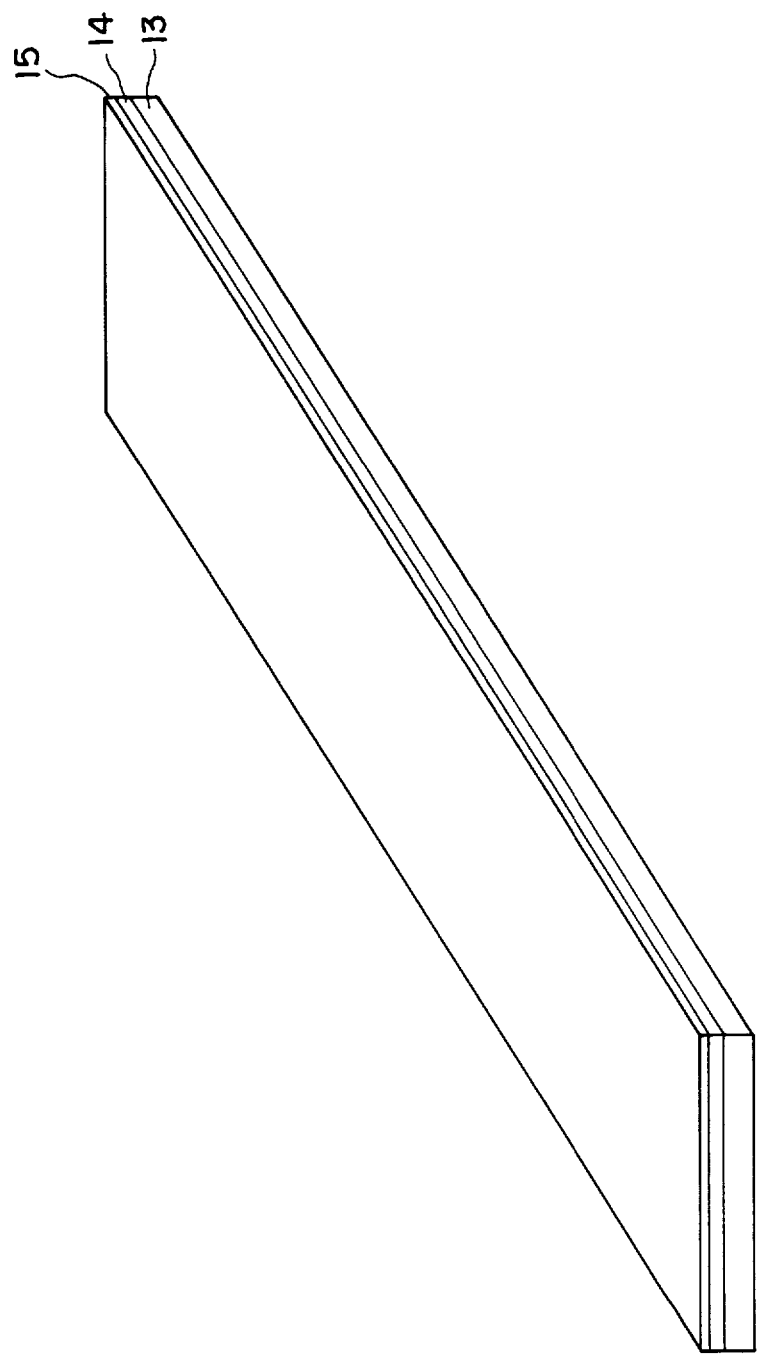
FIG. 6 is a perspective view showing the manufacturing procedures of the ultrasonic probe device according to the first embodiment of the present invention in which acoustic matching layers are formed on an ultrasonic transducer.
Figure 7:
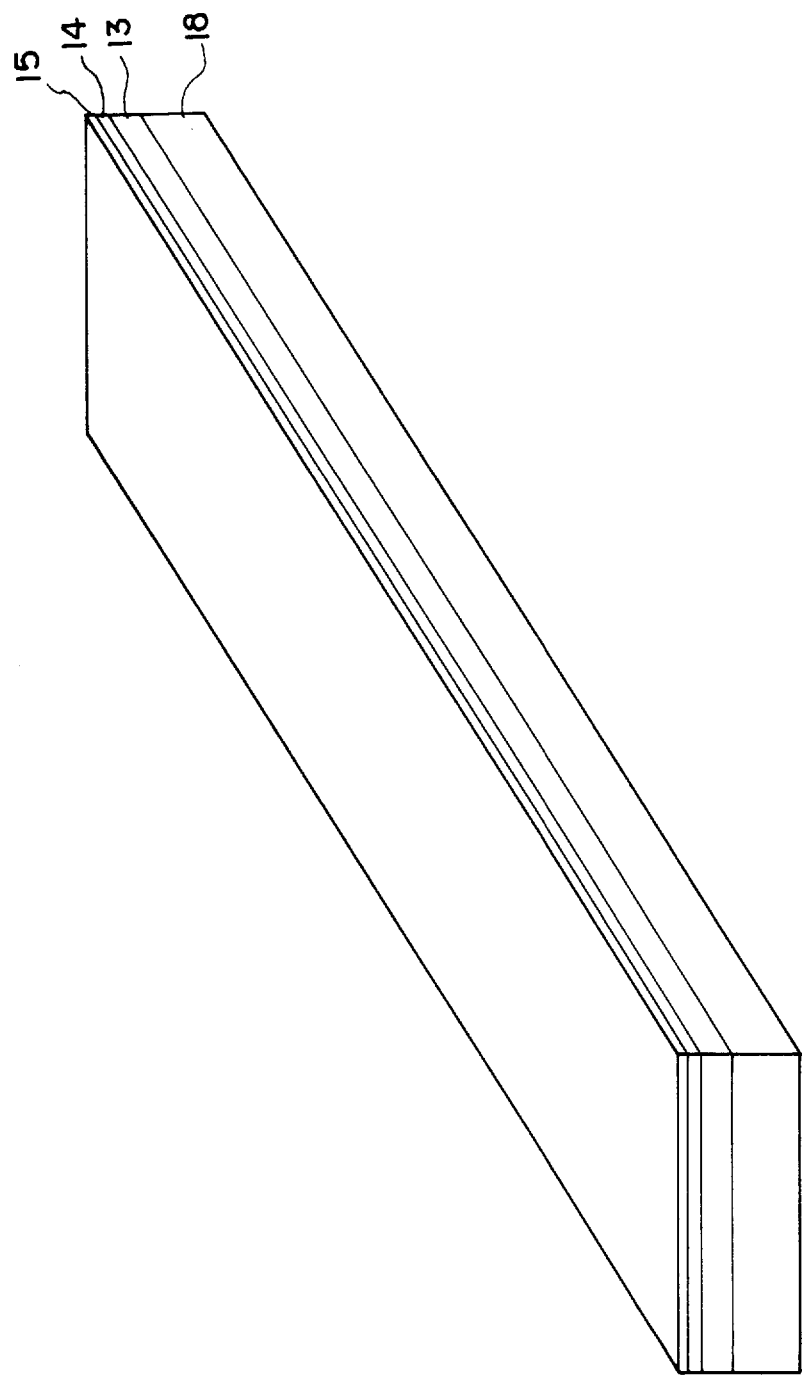
FIG. 7 is a perspective view showing the manufacturing procedures of the ultrasonic probe device according to the first embodiment of the present invention in which a first backing material is formed on the ultrasonic transducer with the acoustic matching layers formed thereon.

First, the plurality of acoustic matching layers 14 and 15 are adhered (joined) to the front surface of the ultrasonic transducer 13 with the signal electrode 20 and the grounding electrode 21 formed on the surface thereof using a heat reaction type film-shaped adhesive, as shown in FIG. 6. Subsequently, the first backing member 18, constituting the first backing layer, is adhered (joined) to the back surface of the ultrasonic transducer 13 using a heat reaction type film-shaped adhesive, as shown in FIG. 7. The heat reaction type film-shaped adhesive has the two functions of a simple hot-melt adhesive for temporary adhesion and a thermosetting type adhesive. The first backing member 18 may be joined first before the acoustic matching layers 14 and 15 are joined.

Figure 8:
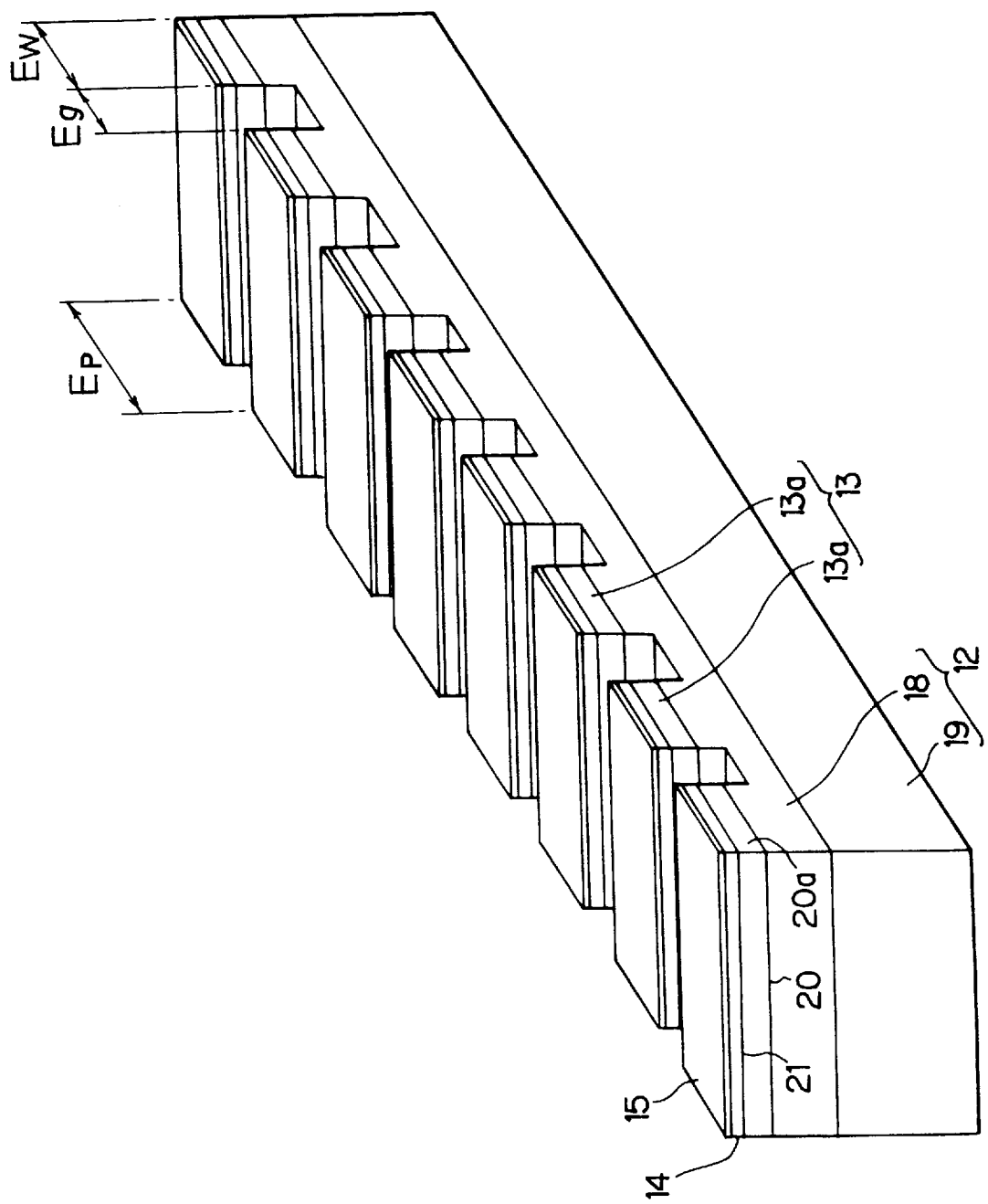
FIG. 8 is a perspective view showing the manufacturing procedures of the ultrasonic probe device according to the first embodiment of the present invention in which the ultrasonic transducer is divided into transducer elements.

The ultrasonic transducer 13 to which the acoustic matching layers 14 and 15 and the first backing member 18 are fixed using the heat reaction type film-shaped adhesive is cut from the front surface side thereof on which the acoustic matching layers 14 and 15 are formed along a longitudinal direction (a direction in which the patient P is sliced; the direction is called a slice direction) of the ultrasonic transducer 13 at a predetermined pitch and at a predetermined depth using a dies, as shown in FIG. 8. Accordingly, an array of the plurality of fine piezoelectric elements (transducer elements) 13a are formed on the first backing member. The plurality of arrayed transducer elements 13a constitute the group of transducer elements. The dies cutting pitch is set to a value which ensures that a width Ew of the transducer element 13a is 70 $\mu$m, that a gap Eg between the adjacent transducer elements is 30 $\mu$m, and in that the element pitch Ep is 100 $\mu$m. The dies cutting depth is adequately set with the thickness of the first backing member 18 taken into consideration. After the plurality of transducer elements 13a are formed on the first backing member 18 to constitute the group of transducer elements, the first backing member 18 is jointed to the second backing member 19 or the backing layer holder constituting the reinforcing layer. Consequently, the transducer element group is reinforced, and stably held. For instance, a heat reaction type film-shaped adhesive is used for joining between the first and second backing members 18 and 19.

Thus, the ultrasonic transducer 13, which is divided into the fine transducer elements 13a at the element with Ew of 70 $\mu$m, at the gap of Eg of 30 $\mu$m and at the element pitch Ep of 100 $\mu$m, is formed on the backing member 12, as shown in FIG. 8.

When the transducer elements 13a are formed, it is considered that the accuracy with which the element pitch is formed is affected by thermal expansion of the backing member 12. However, because of using a thin first backing member 18 in the backing member, cooling property and hence element pitch forming accuracy are improved. If the upper limit of the thickness of the first backing member 18 is 5 mm (if the thickness of the first backing member 18 is 5 mm or below), variations in the element pitch can be eliminated in most of the cases, although it differs depending on the use conditions of the ultrasonic probe device and the material of the backing member.

In the state shown in FIG. 8, the exposed pattern 23 of the FPC 22 is joined to the electrode extending portions 20a formed on one lateral side surfaces which are along the slice dirrection of each of the transducer elements 13a of the ultrasonic transducer 13 by soldering. The conductor pattern (the exposed pattern 23) of the FPC 22 is formed beforehand at a pitch corresponding to the cutting pitch of the transducer 13. As a result, the FPC 22 is connected to one lateral side surfaces of each of the transducer elements 13a of the ultrasonic transducer 13 (see FIG. 9).

Figure 10:
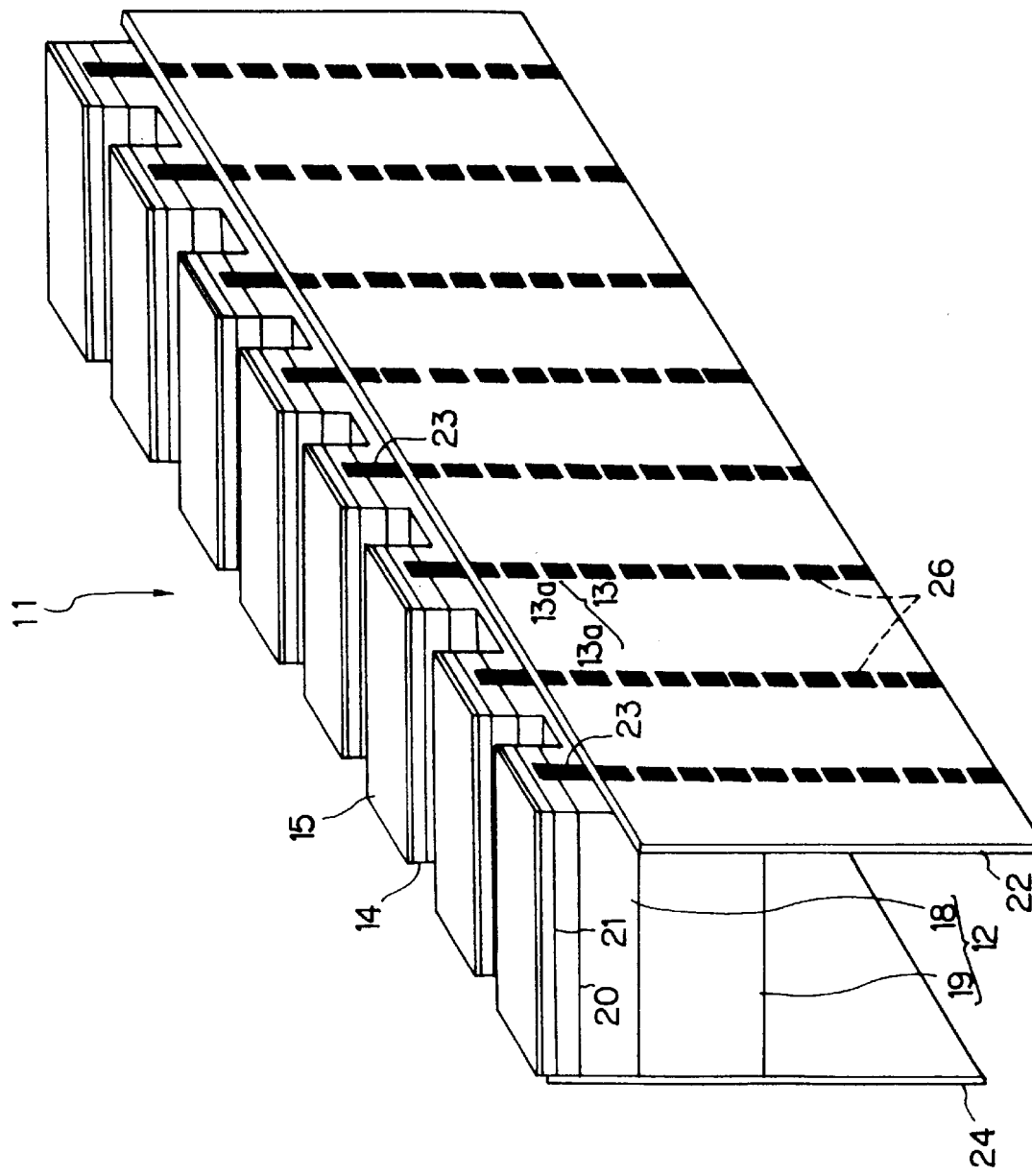
FIG. 10 is a perspective view showing the manufacturing procedures of the ultrasonic probe device according to the first embodiment of the present invention in which the flexible printed circuit and a grounding plate are joined to the ultrasonic transducer.

After the FPC 22 has been connected to one lateral side surface of each of the transducer elements 13a of the ultrasonic transducer 13, the grounding plate 24, serving as the electrode plate, is joined to the grounding electrode extending portions 21a formed on the other lateral side surfaces of each of the transducer elements 13a of the ultrasonic transducer 13 by soldering, as shown in FIG. 10. As a result, the grounding plate 24 is connected to the other lateral side surfaces of each of the transducer elements 13a of the ultrasonic transducer 13.

Figure 9:
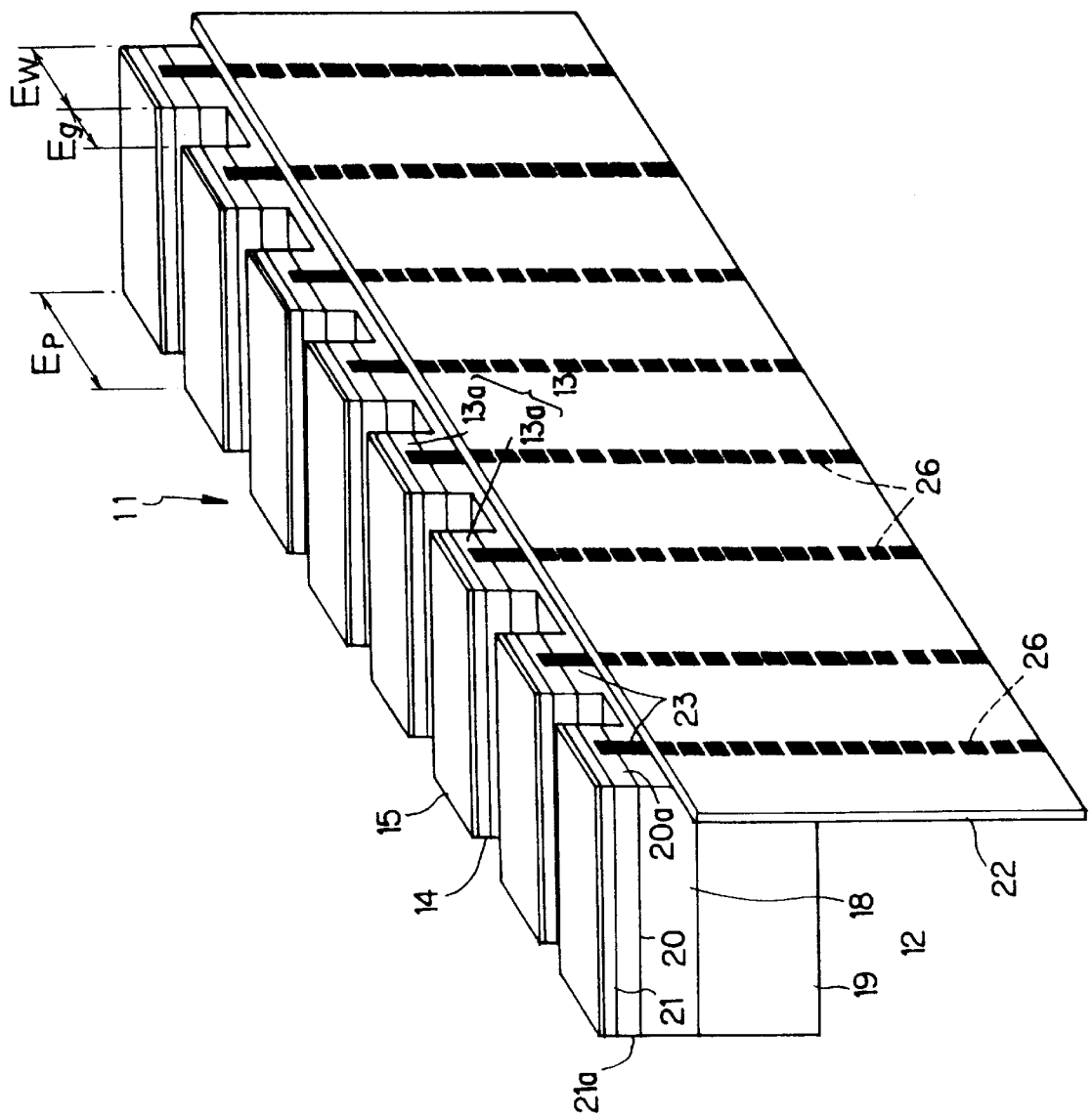
FIG. 9 is a perspective view showing the manufacturing procedures of the ultrasonic probe device according to the first embodiment of the present invention in which a flexible printed circuit is joined to the ultrasonic transducer.
Figure 11:
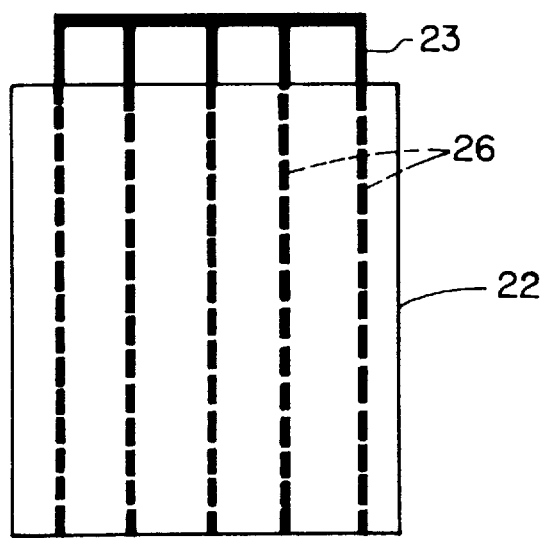
FIG. 11 illustrates an example of the flexible printed circuit joined to the ultrasonic transducer.

The order of the manufacturing processes shown in FIGS. 8 to 10 is changeable. That is, joining of the FPC 22 to the ultrasonic transducer 13 and then cutting of the array of ultrasonic transducer elements 13a by a dies may be performed in that order. In that case, cutting must be performed according to the pattern pitch of the FPC 22. However, pattern joining can be readily performed on the plurality of elements at the same time. In this case, an ordinarily used FPC 22 having a pattern having a common distal end, as shown in FIG. 11, can be used.

Figure 12:
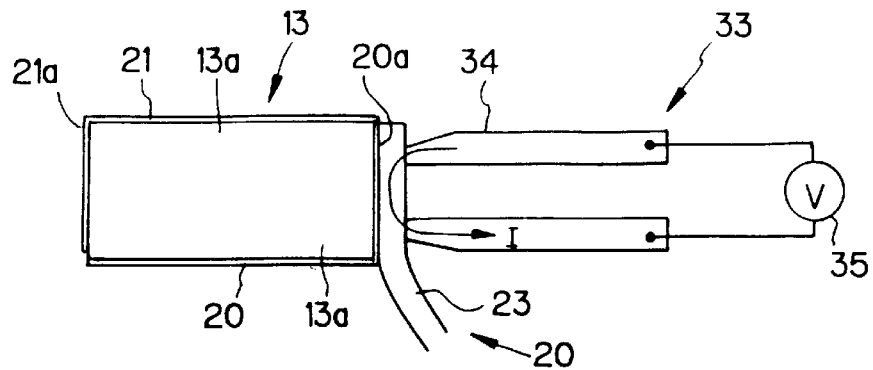
FIG. 12 illustrates joining of the flexible printed circuit (electrode plate) to the side surface of the ultrasonic transducer by the resistance welding method.

Soldering of the FPC 22 to the lateral side surfaces of each of the transducer elements 13a of the ultrasonic transducer 13 is performed by a resistance welding machine 33 shown schematically in FIG. 12. The resistance welding machine 33 is a welding machine which employs the resistance welding method which is the microsoldering technique. The resistance welding machine 22 has a welding chip 34 for resistance welding by parallel gap.

Soldering which employs the resistance welding method by parallel gap is performed in the manner described below: first, the exposed pattern 23 on which plating is performed beforehand is brought into contact with the electrode extending portions 20a. Thereafter, the welding chip 34 of the parallel gap is brought into contact with the exposed pattern 23 and then a voltage E of several volts is applied from a power source 35. Accordingly, a current I flows from the exposed pattern 23 through the electrode extending portions 20a on the lateral side surfaces of each of the transducer elements 13a of the ultrasonic transducer 13, generating Joules heat from the exposed pattern 23 on the basis of the current I. Consequently, plating re-flows, causing the exposed pattern 23 to be soldered to the electrode extending portions 20a.

When soldering is performed, the exposed pattern 23 of the FPC 22 is plated. This plating is performed to a thickness of 3 to 20 $\mu$m. If plating is performed too thin, i.e., to a thickness of less than 3 $\mu$m, the FPC 22 cannot be attached enough to the electrode extending portions 20a of each of the transducer elements 13a of the ultrasonic transducer 13. If plating is conducted to a thickness greater than 20 $\mu$m, there is the possibility that short-circuiting occurs between the adjacent transducer elements 13a. Thus, to solder the exposed pattern 23 to the transducer elements 13a excellently and to perform joining which is free from short-circuiting in the FPC pattern, the thickness of plating is set between 3 and 20 $\mu$m.

Figure 13:
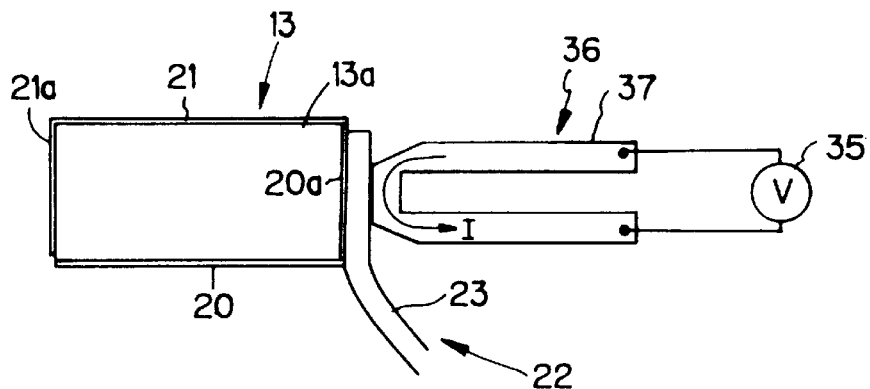
FIG. 13 illustrates joining of the flexible printed circuit board to the side surface of the ultrasonic transducer by the pulse heat heating method.
Figure 14:
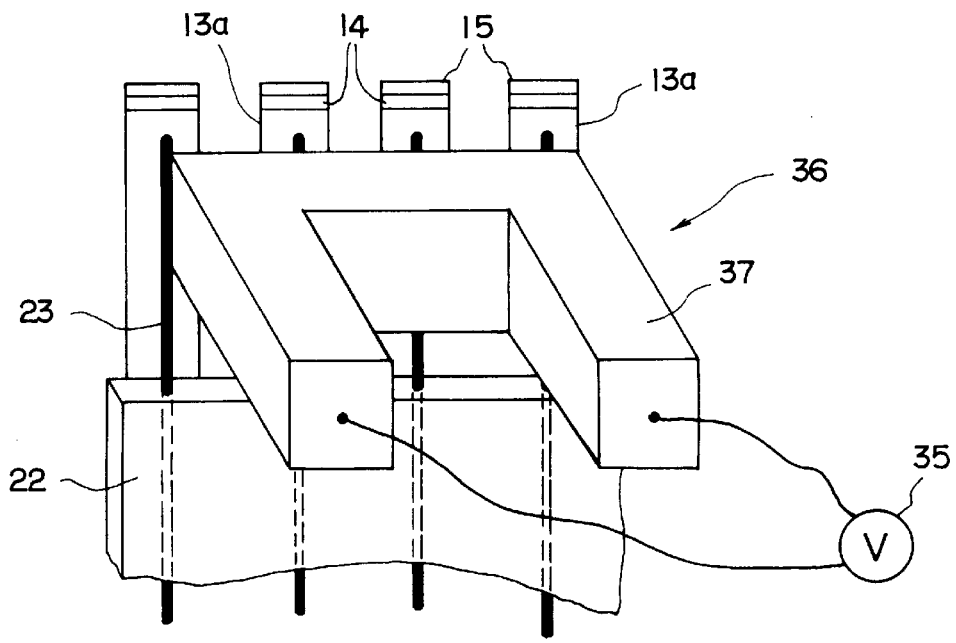
FIG. 14 illustrates joining of the flexible printed circuit board to the side surfaces of the plurality of transducer elements of the ultrasonic transducer by the pulse heat heating method.

Soldering of the FPC 22 to the lateral side surfaces of each of the transducer elements 13a of the ultrasonic transducer 13 may also be performed by the pulse heat heating method shown in FIG. 13.

A pulse heat heating device 36 has a U-shaped heating chip 37.

Soldering employing the pulse heat heating method is performed in the manner described below: first, the exposed pattern 23 on which plating has been performed beforehand is brought into contact with the electrode extending portions 20a. Thereafter, the heating chip 37 is brought into contact with the exposed pattern 23 and then a voltage E is applied from a power source 35. Accordingly, a current I flows in the heating chip 37, generating Joules heat on the basis of the current I due to heating by the resistance of the heating chip 37 itself. Consequently, plating re-flows, causing the exposed pattern 23 to be soldered to the electrode extending portions 20a.

When the pulse heat heating device 36 is used, a plurality of, for instance, four, transducer elements 13a can be soldered and joined to the four signal lines of the exposed pattern 23 of the FPC 22 at the same time. In this embodiment, plating is performed on the exposed pattern 23 of the FPC 22. It may also be conducted on the electrode extending portions 20a.

After the FPC 22 and the grounding plate 24 are adhered (joined) by soldering to the one lateral side surfaces of the respective transducer elements 13a of the ultrasonic transducer 13 and the other lateral side surfaces thereof, respectively, a filler (not shown), such as silicon adhesive serving as an insulating resin material, is filled in the gap of the adjacent transducer elements 13a as an insulating resin material. After a silicon adhesive 39 has been filled, the acoustic lens 16 is provided on the acoustic matching layers 14 and 15, whereby the ultrasonic probe 11 is constituted. The ultrasonic probe 11 is assembled in a probe (casing) at the distal end thereof to constitute the probe head 10. The other end portion of the FPC 22 is connected to the transmitting/receiving circuit via a connector which is not shown and a cable 4a shown in FIG. 1, whereby manufacture of the ultrasonic probe device 4 (as shown in FIG. 1) is almost completed.

In this embodiment, when the FPC 22 and the grounding plate 24 are connected to the ultrasonic transducer 13 for interconnection, joining of the FPC 22 and grounding plate 24 is performed by soldering after the ultrasonic transducer 13 has been divided into the large number of transducer elements 13a. That is, since the FPC 22 and the grounding plate 24 are not yet joined at the time of division of the transducer 13 into the transducer elements 13a, division can be performed effectively and smoothly, thus eliminating a problem involving electrode peel-off.

Further, since soldering between the lateral side surfaces of each of the transducer elements 13a and the FPC 22 is performed by the resistance welding method by parallel gap or the pulse heat heating method, heating can be performed only on the soldering portion during pressurization without warming the parts located around the transducer. Thus, excellent joining is obtained, and generation of thermal expansion and deterioration of the characteristics of the parts can be effectively prevented.

In direct joining of the FPC 22 and the grounding plate 24 to the lateral side surfaces of each of the transducer elements 13a of the ultrasonic transducer 13 by soldering, the transducer side surfaces being not soiled by an adhesive is essential. In the ultrasonic probe 11, since not a liquid adhesive but a film-shaped adhesive is used to form the backing member 12 and acoustic matching layers 14 and 15 on the ultrasonic transducer 13, the possibility that the side surfaces of the transducer would be soiled by the adhesive is eliminated. Thus, excellent soldering is obtained.

A second embodiment of the ultrasonic probe device according to the present invention will be described below with reference to FIGS. 15 to 17.

Figure 15:
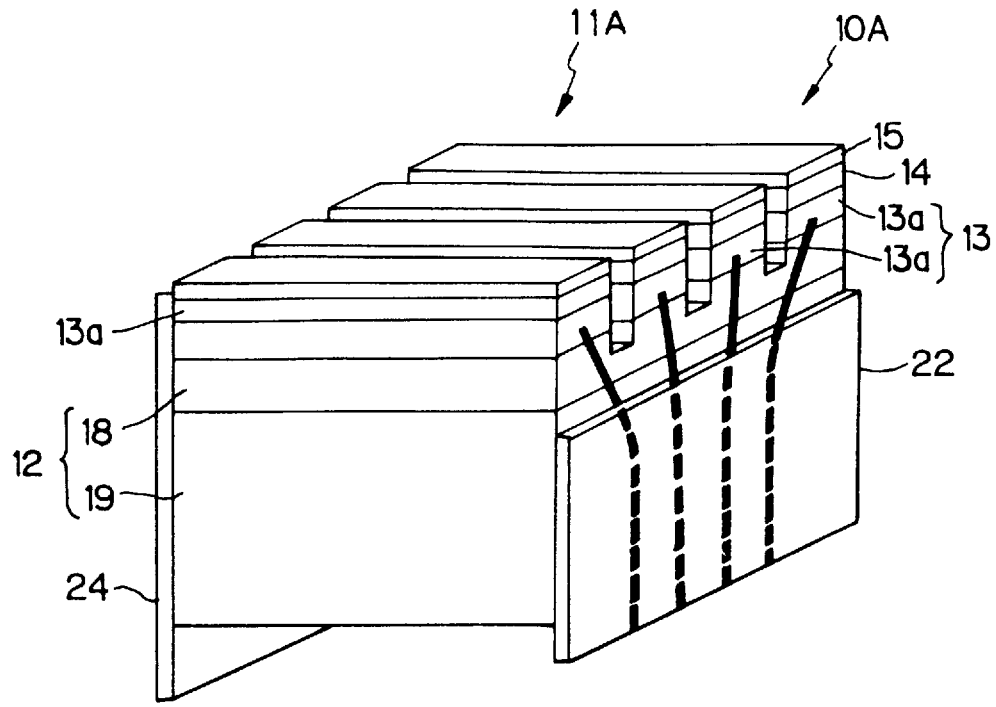
FIG. 15 is a perspective view of a probe head with an acoustic lens removed therefrom, showing a second embodiment of the ultrasonic probe device according to the present invention.

FIG. 15 is an enlarged perspective view illustrating a state where an acoustic lens is removed from the probe head 10A of the ultrasonic probe device. In an ultrasonic probe 11A provided in a probe head 10A, the connection structure of the ultrasonic transducer 13 to the FPC 22 basically differs from the connection structure in the ultrasonic probe 11. The other structure is substantially the same as that of the ultrasonic probe 11 shown in FIG. 2, description thereof being omitted.

The ultrasonic probe 11A shown in FIG. 15 is manufactured by substantially the same procedures as those shown in FIGS. 6 to 10. More specifically, as shown in FIGS. 6 and 7, the plurality of acoustic matching layers 14 and 15 are joined to the front surface of the ultrasonic transducer 13 with the signal electrode and the grounding electrode formed on the surface thereof, and then the first backing member 18 is joined to the back surface of the ultrasonic transducer 13.

In a state where the acoustic matching layers 14 and 15 and the first backing member 18 are joined to the ultrasonic transducer 13, the ultrasonic transducer 13 is cut along the slice direction and divided into the transducer elements 13a which are fine piezoelectric elements, as shown in FIG. 8. That is, the ultrasonic transducer 13 is divided into the fine transducer elements 13a on the plate-like first backing member 18 having a thickness of 5 mm or below to form the group of transducer elements which are the arrayed transducer elements 13a.

Figure 16:
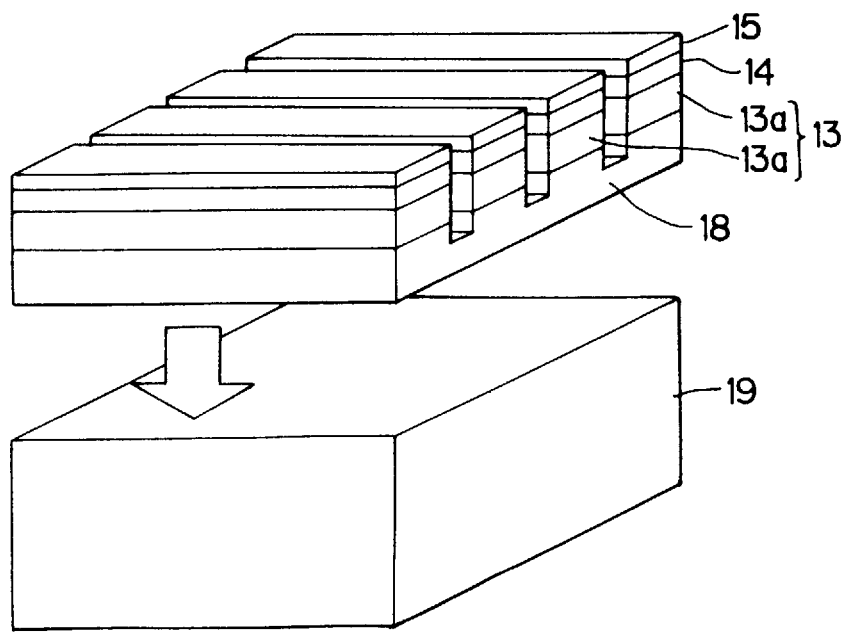
FIG. 16 is a perspective view showing adhesion of an ultrasonic transducer onto a second backing material or a backing layer holder after division of the ultrasonic transducer into transducer elements.

After division, the first backing member 18 is adhered onto the second backing member 19, as shown in FIG. 16. Thereafter, the FPC 22 and the grounding plate 24 are respectively joined by soldering to the one lateral side surfaces and the other lateral side surfaces of each of the transducer elements 13a of the ultrasonic transducer 13 to constitute connection structure.

Figure 17:
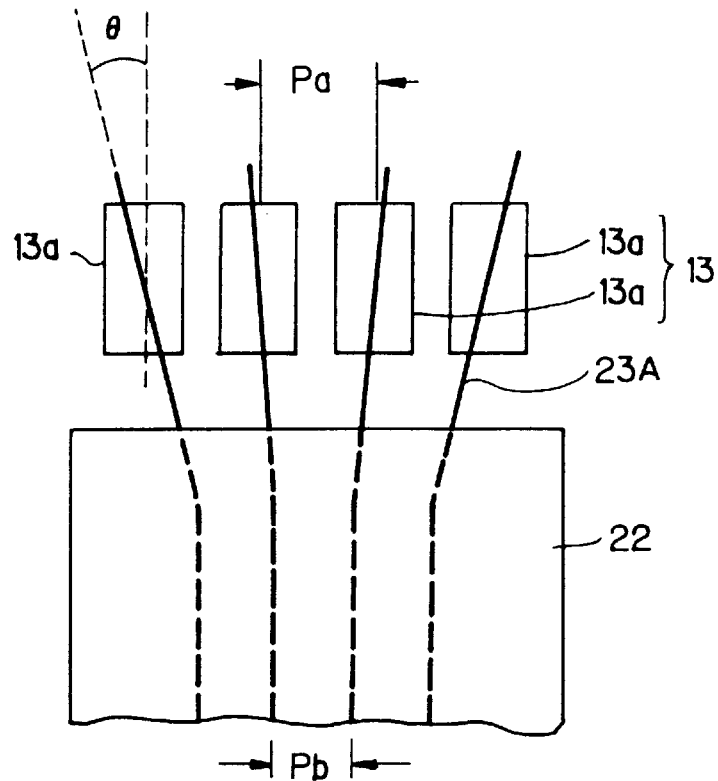
FIG. 17 illustrates another example of a structure of joining the flexible printed circuit to the ultrasonic transducer.

Joining of the FPC 22 to each of the transducer elements 13a of the ultrasonic transducer 13 is performed in the manner shown in FIG. 17. Signal electrode lines constituting an exposed pattern 23A of the FPC 22 to be joined to the transducer elements 13a run in such a manner that the exposed pattern opens in a fan-like shape. In the exposed pattern 23A opened in a fan-like shape, it is possible to absorb deviations generated between the transducer element arrayed pitch Ep of the ultrasonic transducer 13 and the conductor pattern pitch Pb of the FPC 22.

In the fan-shaped exposed pattern 23A of the FPC 22, variations of the pattern pitch thereof are allowed for to some extent. Regarding, for instance, the transducer element 13a on the left in FIG. 16, the signal electrode line of the exposed pattern 23A of the FPC 22 crosses the normal on the transducer element surface at an angle . Thus, even if the element pitch Ep of the transducer elements 13a differs from the pattern pitch Pb of the FPC 22, that difference in the pitch can be absorbed.

The element pitch (channel pitch) Ep of the transducer elements 13a may deviate from the pattern pitch (channel pitch) Pb of the FPC 22 depending on the accuracy with which the transducer elements 13a of the ultrasonic transducer are formed or the accuracy with which the FPC 22 is formed. According to the ultrasonic probe shown in FIGS. 15 to 17, since the signal electrode line of the exposed pattern 23A of the FPC 22 is inclined to the direction of the normal on the transducer element surface of the ultrasonic transducer 13, variations in the pattern pitch Pb of the FPC 22 are allowed for. As a result, in addition to the effects of the first embodiment, absorption of the pitch deviations is possible in the second embodiment.

Figure 18:
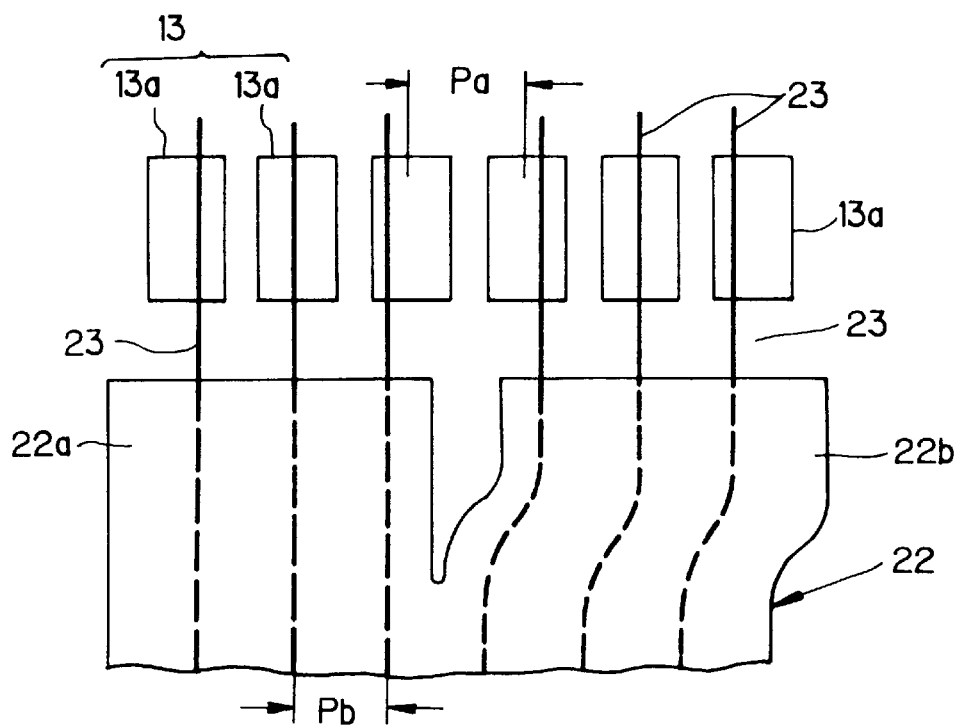
FIG. 18 illustrates another example of a structure of joining the flexible printed circuit to the ultrasonic transducer.

The signal electrode lines of the exposed pattern 23 of the FPC 22 joined to one side surface of the ultrasonic transducer 13 of the ultrasonic probe device may be divided in the manner shown in FIG. 18.

In the structure shown in FIG. 18, the exposed pattern 23 of the FPC 22 is not diffused but the exposed pattern side of the FPC 23 is notched and divided into a plurality of portions. The exposed pattern 23 is effectively joined to the transducer elements 13a of the ultrasonic transducer 13 by soldering utilizing divided portions 22a and 22b generated by division to achieve interconnection of the ultrasonic transducer 13. This structure is also effective to eliminate deviations between the pattern pitch Pb of the FPC 22 and the element pitch Ep of the ultrasonic transducer 13, as in the above-described case.

In place of division of the exposed pattern side of the FPC 22 into a plurality of portions, the FPC 22 may be divided into a plurality of portions. The exposed pattern 23 of each of the FPC 22 portions is joined to the lateral side surfaces of the transducer elements 13a of the ultrasonic transducer 13 by soldering. Deviations between the pattern pitch Pb of the FPC 22 and the element pitch Ep of the ultrasonic transducer 13 can be eliminated by using the plurality of FPC portions 22.

Figure 19:
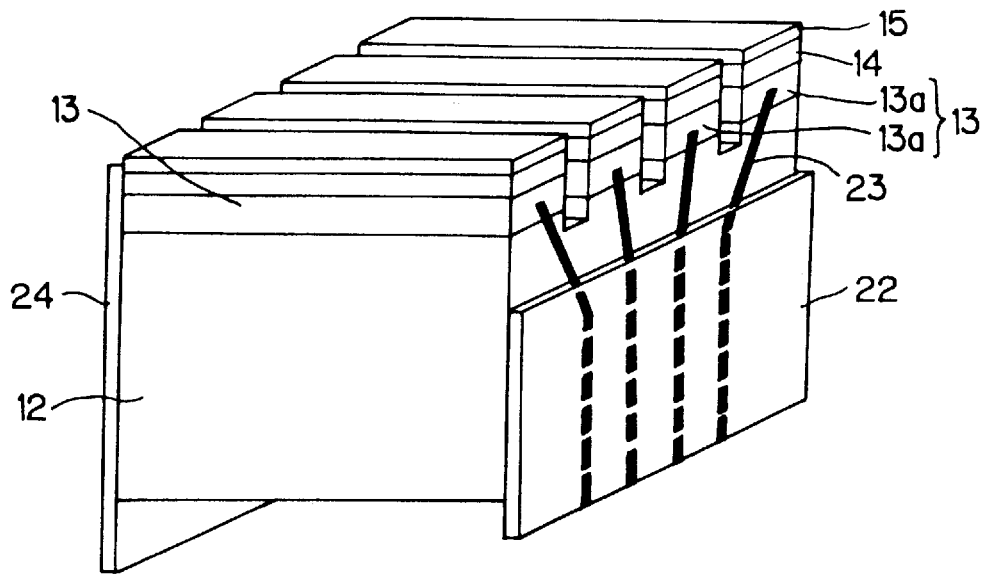
FIG. 19 is a perspective view showing a modification of the ultrasonic probe device shown in FIG. 15.

FIG. 19 shows a modification of the ultrasonic probe device shown in FIG. 15. While FIG. 15 shows a structure in which the backing member 12 for supporting the ultrasonic transducer 13 is constituted by joining the first and second backing members 18 and 19, FIG. 19 shows a structure in which a single-layer backing member 12 supports the ultrasonic transducer 13. The other structure is the same as that of the ultrasonic probe device shown in FIG. 15, description thereof being omitted.

Figure 20:
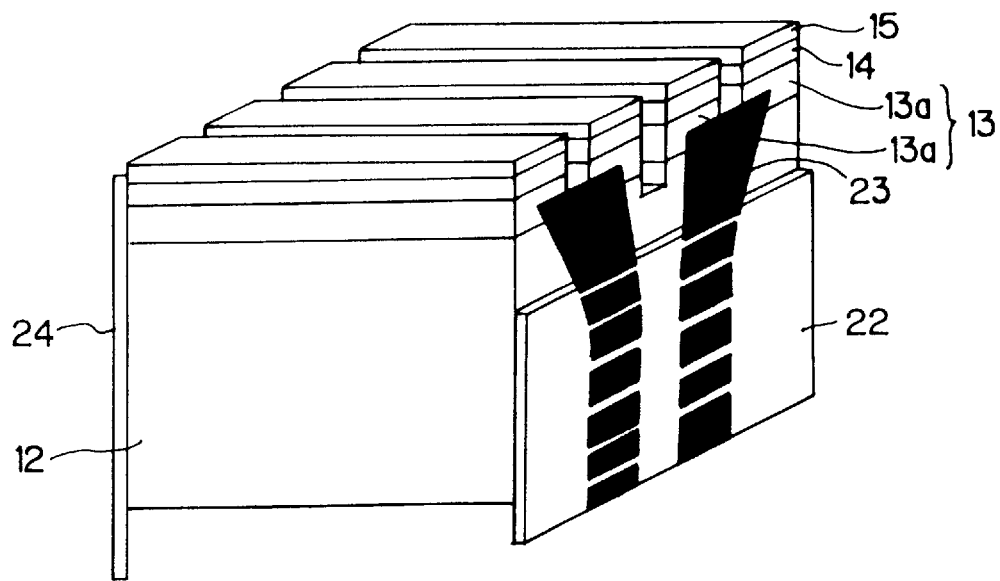
FIG. 20 is a perspective view showing a third embodiment of the ultrasonic probe device according to the present invention.

FIG. 20 shows a third embodiment of the ultrasonic probe device according to the present invention.

The ultrasonic probe of this embodiment is a linear type probe having sub-dies. In this structure, the signal electrode line of the exposed pattern 23 of the FPC 22 is jointed to a plurality of transducer elements, e.g., two transducer elements 13a in this embodiment, in the group of transducer elements of the ultrasonic transducer 13 by soldering.

Figure 21:
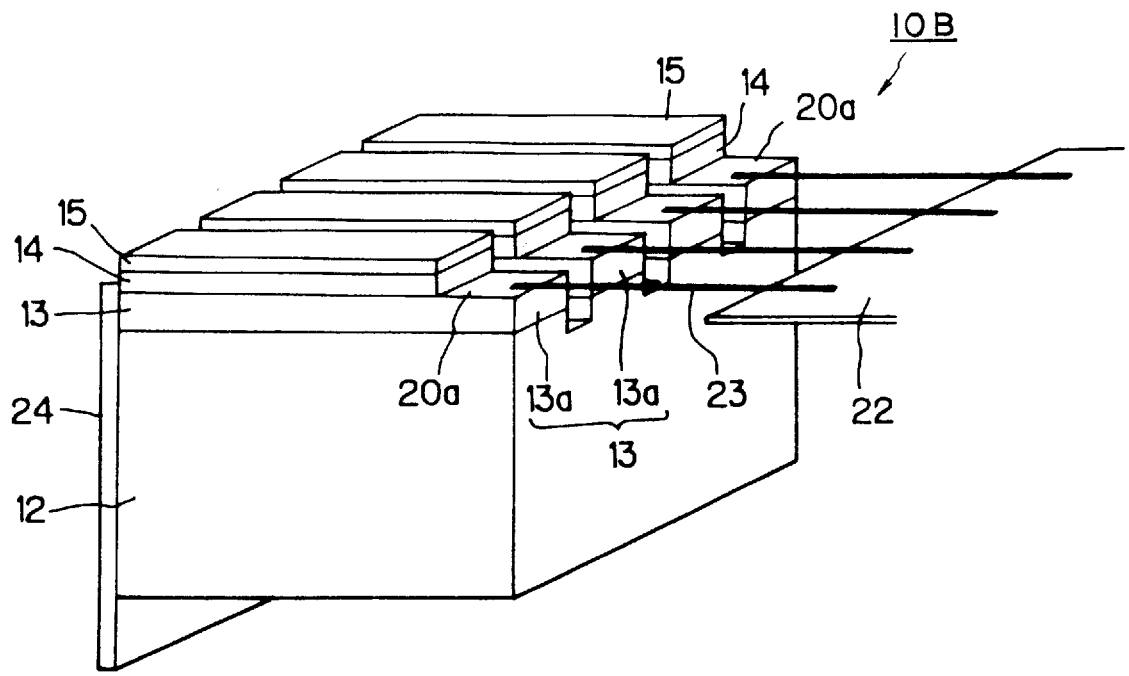
FIG. 21 is a perspective view showing a fourth embodiment of the ultrasonic probe device according to the present invention.
Figure 22:
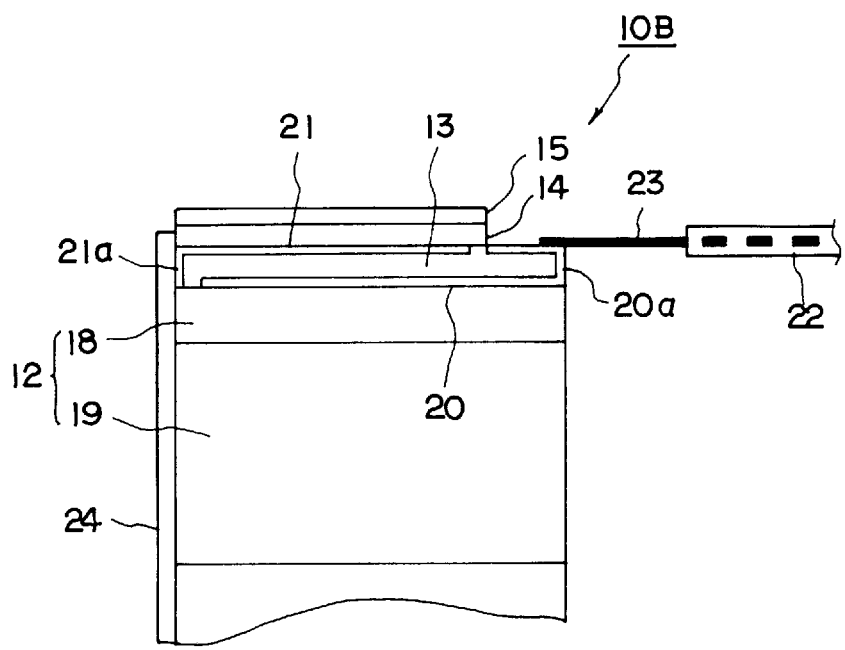
FIG. 22 is a side elevational view of the ultrasonic probe incorporated in the ultrasonic probe device shown in FIG. 21.

FIGS. 21 and 22 show a fourth embodiment of the ultrasonic probe device according to the present invention.

In the ultrasonic transducer 13 of an ultrasonic probe 10B of the ultrasonic probe device according to this embodiment, the signal electrode 20 formed on the back surfaces of each of the transducer elements 13a of the ultrasonic transducer 13 extends to one end portion of the front surfaces thereof through the one lateral side surfaces thereof, while the grounding electrode 21 extends from the front surface to the other lateral side surfaces, as shown in FIG. 22. The acoustic matching layers 14 and 15 are formed on the front surfaces of each of the transducer elements 13a of the ultrasonic transducer 13 except for the one end portion thereof. That is, the portion of the signal electrode 20, which is formed on one end portion of the front surface of the ultrasonic transducer 13, is not covered by the acoustic matching layers 14 and 15 and exposed. The exposed pattern 23 of the FPC 22 is joined to the exposed portions of the signal electrodes 20 (the electrode extending portions 20a) of the transducer elements 13a by soldering.

The grounding plate 24, which is an electrode plate, is joined to the grounding electrodes 21 (the grounding electrode extending portions 21a) on the lateral side surfaces of each of the transducer elements 13a of the ultrasonic transducer 13 by soldering. The other structure and effect of the ultrasonic probe 10B are the same as those of the ultrasonic probe according to the first embodiment.

Figure 23:
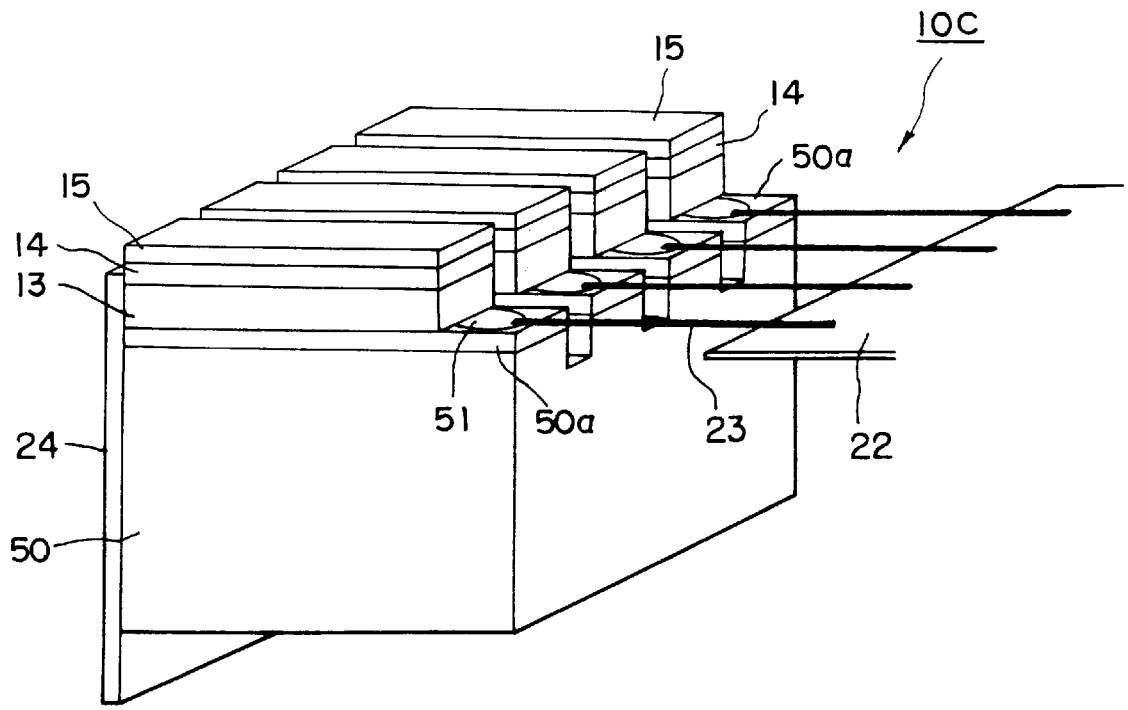
FIG. 23 is a perspective view showing a fifth embodiment of the ultrasonic probe device according to the present invention.
Figure 24:
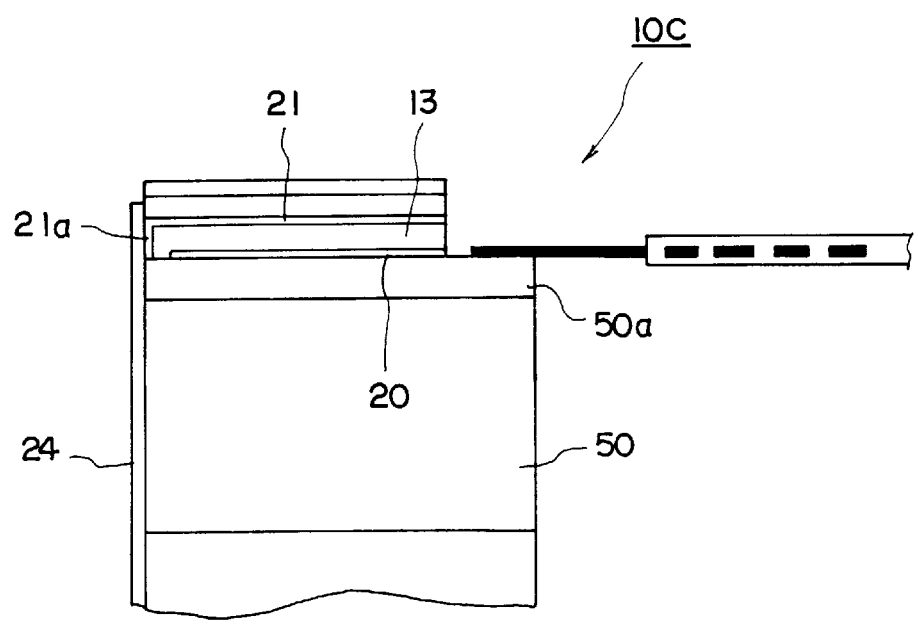
FIG. 24 is a side elevational view of the ultrasonic probe incorporated in the ultrasonic probe device shown in FIG. 23.

FIGS. 23 and 24 show a fifth embodiment of the ultrasonic probe device according to the present invention.

The ultrasonic transducer 13 of an ultrasonic probe 10C of the ultrasonic probe device according to this embodiment is manufactured in the manner described below: first, a square backing member 50 having a predetermined thickness is prepared. The backing member 50 has a conductive pattern 50a having a predetermined pitch formed beforehand on the upper surface (front surface) thereof. The backing member 50 also has a land 51, serving as a signal connecting portion, formed on the upper surface thereof at a predetermined position containing the conductive pattern.

On the other hand, a rectangular flat plate-like ceramic piezoelectric member 13A made of a ceramic, such as lead titanate zirconate porcelain, is prepared. The short side of the piezoelectric member 13A is shorter than the short side of the backing member 50 by a predetermined length. The signal electrode (Au or Ag electrode) 20 is formed on the back surface of the piezoelectric member 13A, and the grounding electrode (Au or Ag electrode) 21 is formed on the front surface of the piezoelectric member 13A. The grounding electrode 21 formed on the front surface thereof to one side surface which is along a longitudinal direction of the piezoelectric member 13A to constitute the ultrasonic transducer 13.

Thereafter, the front surface of the backing member 50 is joined to the back surface of the ultrasonic transducer 13 using, for example, a heat reaction type film-shaped adhesive, whereby the conductive pattern 50a formed on the front surface of the backing member 50 is connected to the signal electrode 20 formed on the back surface of the ultrasonic transducer 13. Subsequently, the plurality of acoustic matching layers 14 and 15 are adhered (joined) to the front surface of the ultrasonic transducer 13 using a heat reaction type film-shaped adhesive. At that time, the end portion of the front surface of the backing member 50 remains exposed (see FIGS. 23 and 24).

Next, the ultrasonic transducer 13 is cut from the front surface side thereof on which the acoustic matching layers 14 and 15 are formed along the conductive pattern formed on the front surface of the backing member 50 at a predetermined pitch in a predetermined depth using a dies to form an array of the plurality of fine piezoelectric elements (transducer elements) 13a on the backing member 50.

The conductive pattern of the FPC 20 and the exposed pattern 23 at the distal end thereof are formed on the FPC 22 beforehand at a pitch corresponding to the pitch of the conductive pattern on the backing member 50. The exposed pattern 23 of the FPC 22 is joined to the lands 51 of the conductive pattern 50a exposed at the end portion of the front surface of the backing member 50 by soldering which utilizes the resistance welding method shown in FIG. 12 or the pulse heat heating method shown in FIG. 13. Accordingly, the FPC 22 is joined to the signal electrodes 20 of the transducer elements 13a through the conductive pattern 50a of the backing member 50 for signal electrode connection (see FIGS. 23 and 24).

After the FPC 22 has been connected to the end portion of the front surface of the backing member 50, the grounding plate 24, serving as the electrode plate, is joined to the grounding electrode extending portions 21a formed on the lateral side surfaces of each of the ultrasonic transducer elements 13a of the ultrasonic transducer 13 by soldering for grounding electrode connection, as shown in FIGS. 23 and 24.

The other structure of the ultrasonic probe 10C is substantially the same as that of the ultrasonic probe according to the first embodiment. In this embodiment, since the exposed pattern 23 of the FPC 22 is joined to the lands 51 including the conductive pattern formed on the backing member 50 for signal electrode connection, connection of the signal electrode is further facilitated. The other effects of the fifth embodiment are the same as those of the first embodiment.

Figure 25:
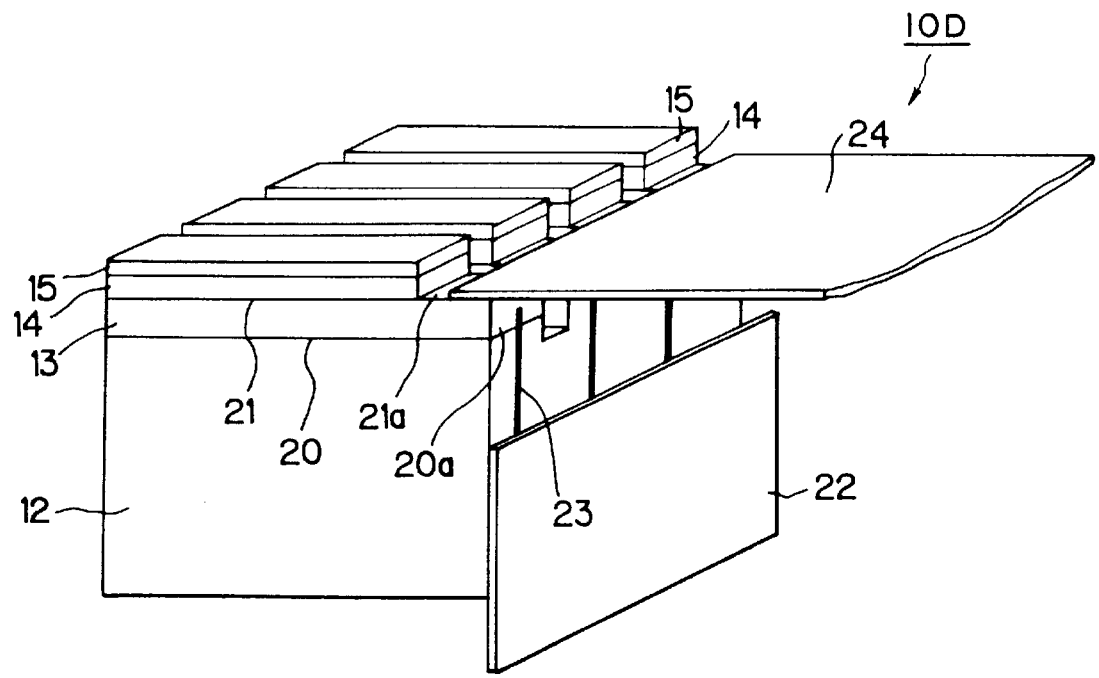
FIG. 25 is a perspective view showing a sixth embodiment of the ultrasonic probe device according to the present invention.
Figure 26:
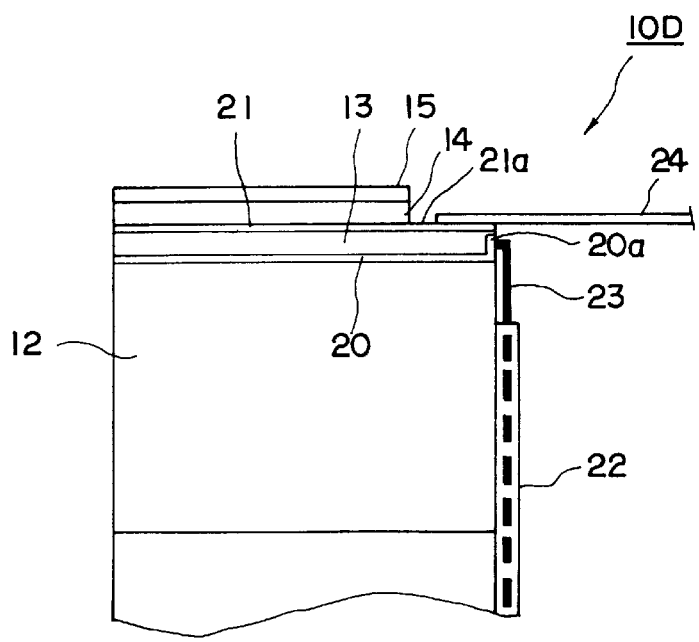
FIG. 26 is a side elevational view of the ultrasonic probe incorporated in the ultrasonic probe device shown in FIG. 25.

FIGS. 25 and 26 show a sixth embodiment of the ultrasonic probe according to the present invention.

In an ultrasonic probe 10D of the ultrasonic probe device according to the sixth embodiment, the FPC 22 and the grounding plate 24 are joined to one side of the ultrasonic transducer 13 by soldering.

In the ultrasonic transducer 13, the grounding electrode 21 is formed on the front surface thereof, and the signal electrode 20 is formed on the back surface of the ultrasonic transducer 13. The signal electrode 20 formed on the back surface thereof extends to the one side surface which is along to a longitudinal dirrection of the ultrasonic transducer 13, as shown in FIG. 26. The acoustic matching layers 14 and 15 are formed on the front surface of the ultrasonic transducer 13 except for one end portion thereof (the grounding electrode 21). That is, the portion of the grounding electrode 21 is not covered by the acoustic matching layers 14 and 15 and remains exposed.

After the ultrasonic transducer 13 is finely divided by a dies to form the large number of arrayed transducer elements 13a, connection of the signal electrode 20 and grounding electrode 21 is performed. For connection of the signal electrodes, the exposed pattern 23 of the FPC 22 is soldered to the signal electrodes 20 (the electrode extending portions 20a) formed on the lateral side surfaces of the respective transducer elements 13a of the ultrasonic transducer 13. Connection of the grounding electrode is performed by joining the grounding plate 24 to the exposed grounding electrodes 21 (the grounding electrode extending portions 21a) of the respective transducer elements 13a of the ultrasonic transducer 13 by soldering. Joining by soldering can be performed utilizing the resistance welding method shown in FIG. 12 or the pulse heat heating method shown in FIG. 13 without generating short-circuiting.

The ultrasonic probe device shown in FIGS. 25 and 26 has an advantage in that the cross-talk between the channels can be reduced in addition to the effects of the first embodiment.

While the sixth embodiment has been shown wherein the grounding electrode 21 is formed on the ultrasonic wave radiating front surfaces of each of the transducer elements 13a of the ultrasonic transducer 13 and the signal electrode 20 is formed on the back surfaces of each of the ultrasonic transducer elements 13a of the ultrasonic transducer 13 and on the one lateral side surface thereof, alternate embodiments might include an ultrasonic probe device wherein the signal electrode and the grounding electrode are formed in a reversed way. In that case, the FPC 22 is jointed to the signal electrodes (the exposed electrodes) on the front surfaces of the respective transducer elements 13a of the ultrasonic transducer 13, and the grounding plate 24 is joined to the grounding electrodes formed on the lateral side surfaces of the transducer elements 13a.

In this modification, if the side extending electrodes on the respective transducer elements 13a of the ultrasonic transducer 13 are formed by deposition, sputtering, baking or plating and if the signal electrodes and grounding electrodes formed on the front and back surfaces of the transducer elements 13a of the ultrasonic transducer 13 are Ag baked electrodes, inexpensive electrodes exhibiting excellent adhesion can be obtained.

The ultrasonic probe devices of the above-described embodiments of the present invention are designed such that the FPC 22 and the grounding plate 24, which are electrode plates, are joined to the ultrasonic transducer 13 by soldering. Interconnection may also be performed in the manners shown in FIGS. 27 and 28.

Figure 27:
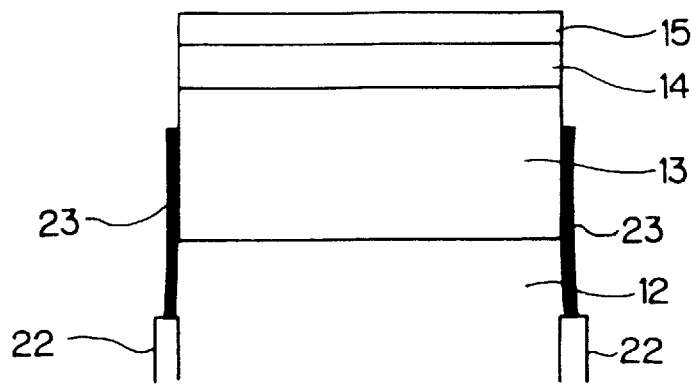
FIG. 27 is a side elevational view showing another example of an interconnection structure of the ultrasonic transducer according to the present invention.

In the ultrasonic probe device shown in FIG. 27, an electrode layer is formed on each of the two lateral side surfaces of the transducer elements 13a of the ultrasonic transducer 13, and the exposed patterns 23 of the FPCs 22 are respectively joined to the electrode layers formed on the two lateral side surfaces of the transducer elements 13a by soldering to achieve interconnection using the two FPCs 22. At that time, one of the FPCs 22 may be utilized as the signal electrode plate while the other FPC 22 may be utilized as the grounding electrode plate. Alternatively, signal lines and the grounding lines may be provided in the electrode layers on the two side surfaces of the transducer elements 13a of the ultrasonic transducer 13 in an adequately mixed state. At that time, the signal lines and grounding lines in the patterns of the FPCs 22 are also formed in a similarly mixed state.

Figure 28:
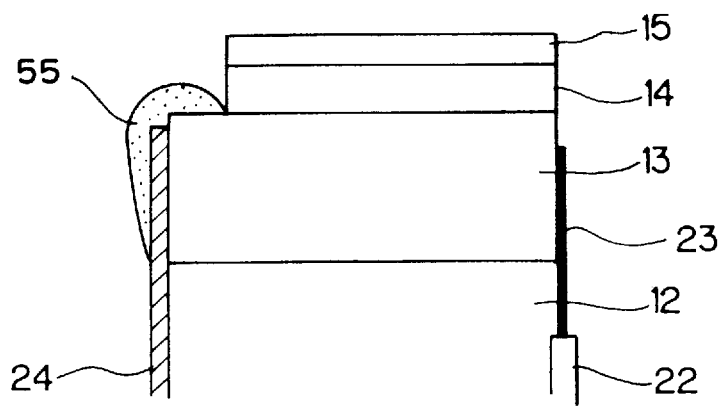
FIG. 28 is a side elevational view showing another example of an interconnection structure of the ultrasonic transducer according to the present invention.
Figure 29:
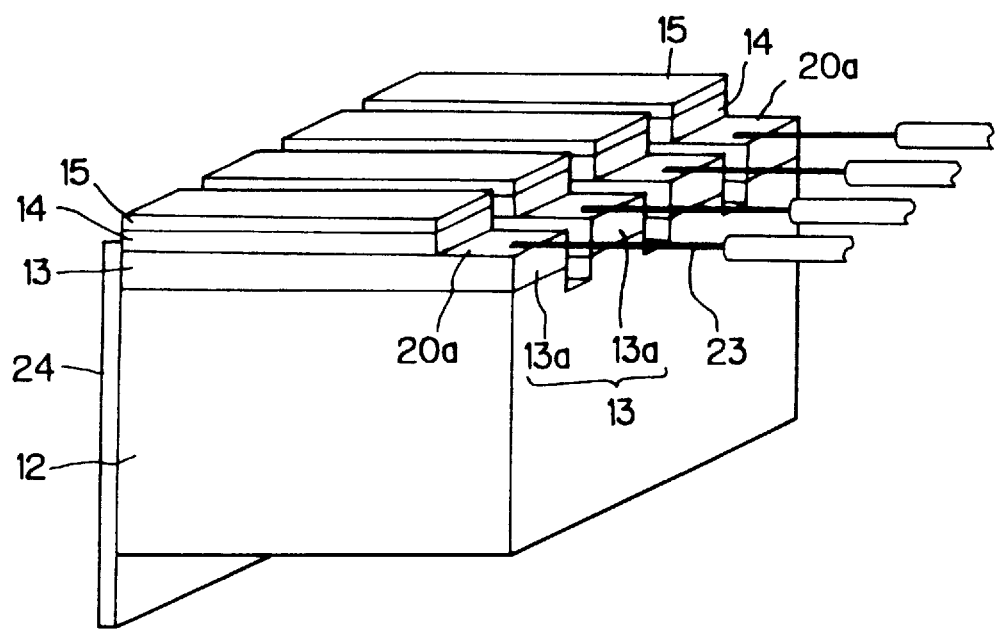
FIG. 29 is a perspective view showing joining of coaxial cables to the electrode layers formed on the front surfaces of the transducer elements.

Alternatively, the exposed pattern of the FPC 22 may be joined by soldering to one of the lateral side surfaces of the transducer elements 13a, while the copper grounding plate 24 may be joined to the other side surfaces thereof using a conductive adhesive 55, as shown in FIG. 28. At that time, the grounding electrode may be formed on an end portion of the front surface of the ultrasonic transducer 13 in an exposed state, and the grounding plate may be joined to that exposed grounding electrode (the grounding electrode extending portion) so as to increase the joining force of the conductive adhesive 55.

There are various other joining methods of joining the FPC 22 and the grounding plate 24 to the ultrasonic transducer 13. In either case, after the ultrasonic transducer 13 has been divided into fine transducer elements, the FPC 22 or the grounding plate 24 is joined to the group of transducer elements. In this way, a troublesome adjusting operation between the cutting positions of the ultrasonic transducer 13 and the pattern of the FPC 22 can be eliminated, and the manufacturing property of the ultrasonic probe devices can thus be improved. Further, since a plurality of ultrasonic probe devices can be continuously cut, productivity is increased.

Further, while the above embodiments employ the FPC 22 having an exposed distal end as the interconnection material for used in signal electrode connection, the present invention is not limited to this. For instance, a plurality of coaxial cables 56 may be used for connection of the electrode extending portions 20a. That is, connection is performed by joining the electrode extending portions 20a formed on the side surface of the transducer elements 13a to the signal line of the coaxial cable 56 by, for example, soldering. In that case, the grounding lines (outer skins) of the coaxial cables 56 are adequately bound. Grounding electrode connection may be performed by joining the grounding line to the grounding electrode.

Figure 30:
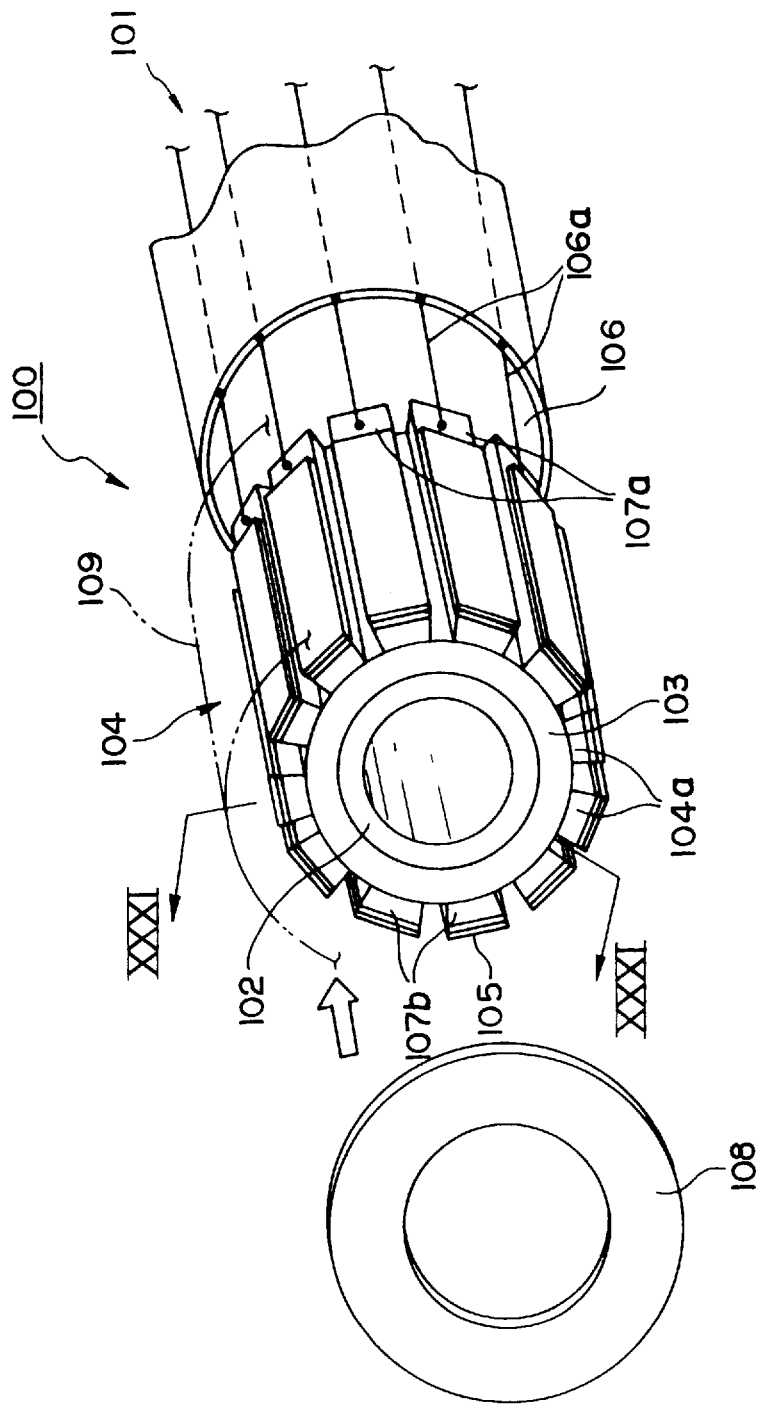
FIG. 30 is a schematic perspective view of an ultrasonic probe incorporated in a probe head according to a seventh embodiment of the present invention.

A seventh embodiment of the present invention will now be described with reference to FIGS. 30 to 35. FIG. 30 is a enlarged schematic perspective view showing a probe head 100 of an ultrasonic probe device according to the seventh embodiment of the present invention. The probe device of this embodiment is a radial scanning type probe device. This embodiment is also applied to ultrasonic probe devices having a curved ultrasonic radiating surface, such as a convex scanning type ultrasonic probe device.

Figure 31:
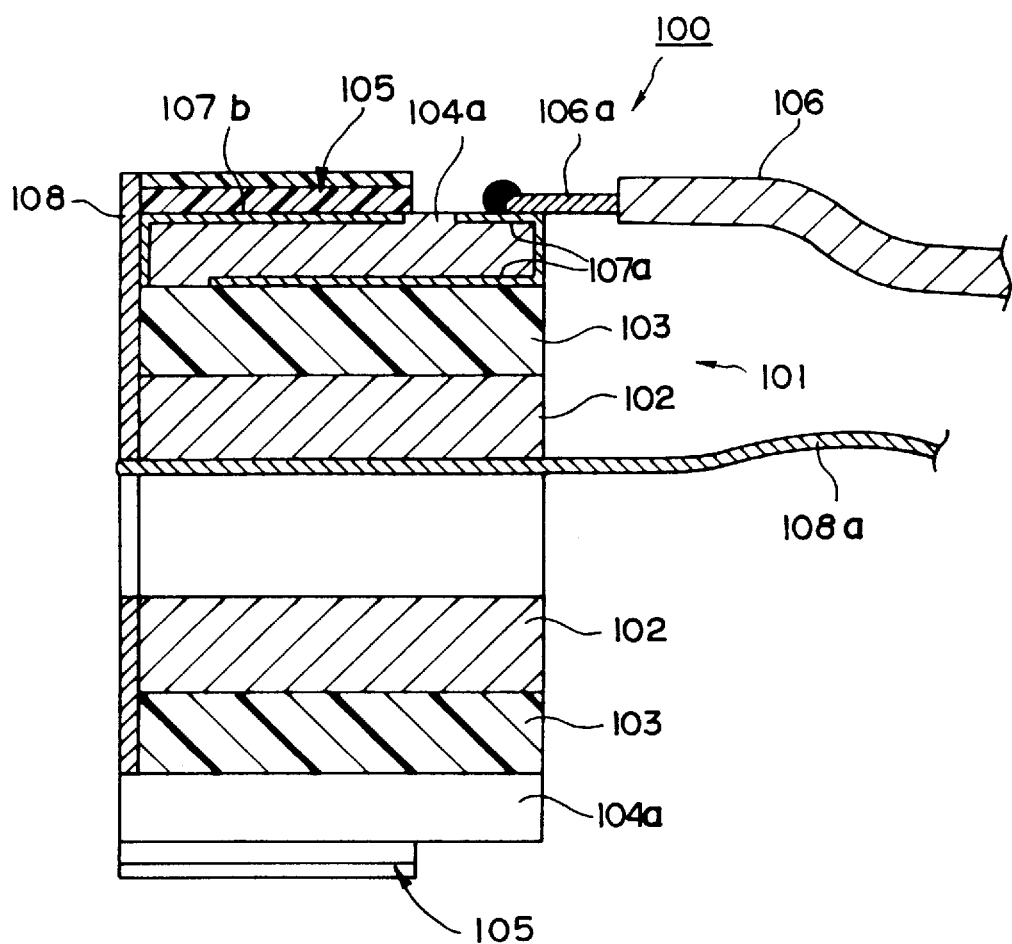
FIG. 31 is a cross-section taken along the line XXXI—XXXI of FIG. 30.

The ultrasonic probe head 100 of the radial type ultrasonic probe device shown in FIGS. 30 and 31 has an ultrasonic probe 101. The ultrasonic probe 101 has a hollow cylindrical container 102. A flexible backing member 103 is adhered to the outer peripheral surface of the container 102 in a curved state. A flat-plate like ultrasonic transducer 104 is adhered to the outer peripheral surface of the backing material 103 in a curved state.

The ultrasonic transducer 104 is made up of transducer elements 104a divided at a predetermined pitch. The transducer elements 104a are arrayed along the central axis direction of the container 102. Acoustic matching layers 105 are formed on greater part of an ultrasonic wave radiating surface (a front surface) of each of the transducer elements 104a so as to readily transmit a signal from the transducer elements 104a (a solid) into an organism (liquid).

An FPC 106 having an exposed conductor pattern (exposed pattern) 106a at a predetermined pitch is wound around the outer peripheral surface of the container 102 in a state wherein it is located close to one side surface of the ultrasonic transducer 104. The exposed end portion of each of the conductors constituting the conductor pattern 106a of the FPC 106 is joined to an electrode layer 107a formed on the front surface of each of the transducer elements 104a beforehand by soldering. The other end of the conductor pattern 106a of the FPC 106 is connected to a transmitting/receiving circuit or the like via a connector and a cable which are not shown.

A grounding plate 108 is adhered by, for example, soldering to the side surface of the ultrasonic transducer 104 which is remote from the FPC 106.

The ultrasonic transducer 104 is covered with an acoustic lens 109.

The ultrasonic probe device having the ultrasonic probe 101 arranged in the manner described above is inserted into a body cavity of a patient for diagnosis. Each of the transducer elements 104a is driven by an electric signal controlled by the transmitting/receiving circuit to output an ultrasonic signal in a radial fashion from the front surface of the transducer element 104a. An ultrasonic signal (echo signal) reflected by, for example, an organ in a body cavity of the patient is received by the transducer element 104a of the ultrasonic probe 101. The ultrasonic signal is sent to a DSC which is not shown via the transmitting/receiving circuit. The ultrasonic signal is converted into an image signal. The image signal is sent to a monitor which is not shown and displayed by the monitor as an ultrasonic image.

The method of manufacturing the above-described ultrasonic probe device will be described below.

First, a substantially rectangular piezoelectric plate 104A made of a ceramic, such as lead titanate zirconate porcelain, is prepared. The ultrasonic transducer plate 104a has an electrode layer 107a for signal lines formed on the front surface thereof and on one longitudinal side surface thereof beforehand. Thus, the electrode layer 107a is continuously formed from the front surface thereof to the one longitudinal side surface thereof. The ultrasonic transducer plate 104A also has an electrode layer 107b for grounding formed on the back surface thereof, on the other longitudinal side surface thereof and part of the front surface thereof beforehand. Thus, the electrode layer 107b is continuously formed from the front surface thereof through the other longitudinal side surface thereof to part of the front surface thereof. The ultrasonic transducer plate 104A with the electrode layers 107a and 107b formed thereon constitutes the ultrasonic transducer 104. The electrode layers formed on the individual transducer elements of the ultrasonic transducer are, for instance, Au or Ag electrodes, as in the case of the first embodiment. These electrode layers are formed in either of the methods shown in FIGS. 5(A), 5(B) and 5(C).

Figure 32:
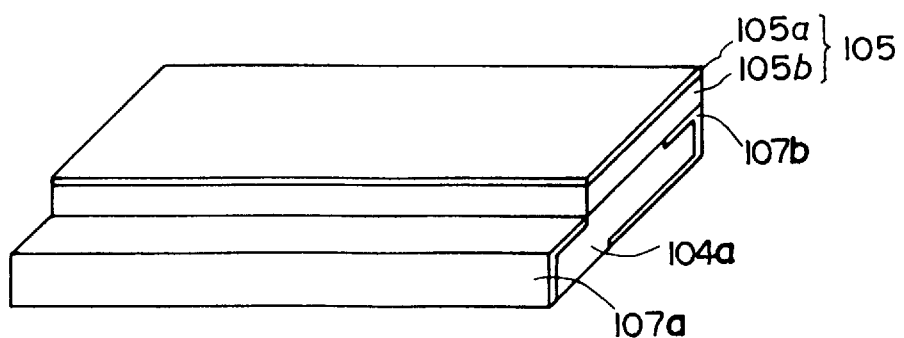
FIG. 32 is a perspective view showing the manufacturing procedures of the ultrasonic probe device according to the seventh embodiment of the present invention in which acoustic matching layers are formed on an ultrasonic transducer.

Next, the plurality of acoustic matching layers 105 (105A, 105B) are adhered to the portion of the front surface of the ultrasonic transducer 104 where no electrode layers are formed using a heat reaction type film-shaped adhesive, as shown in FIG. 32.

Figure 33:
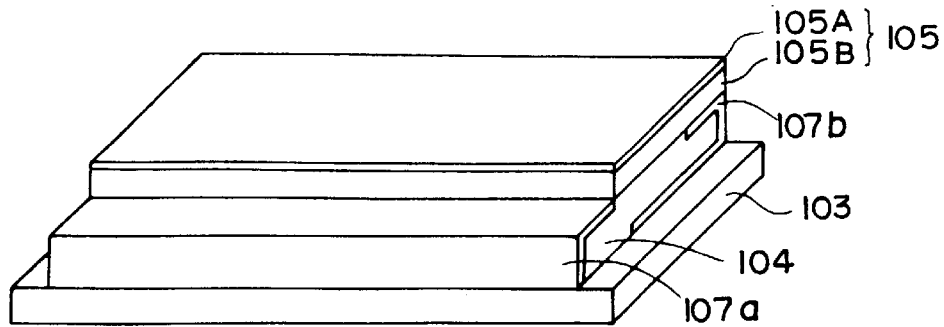
FIG. 33 is a perspective view showing the manufacturing procedures of the ultrasonic probe device according to the seventh embodiment of the present invention in which a backing member is formed on the ultrasonic transducer with the acoustic matching layers formed thereon.
Figure 34:
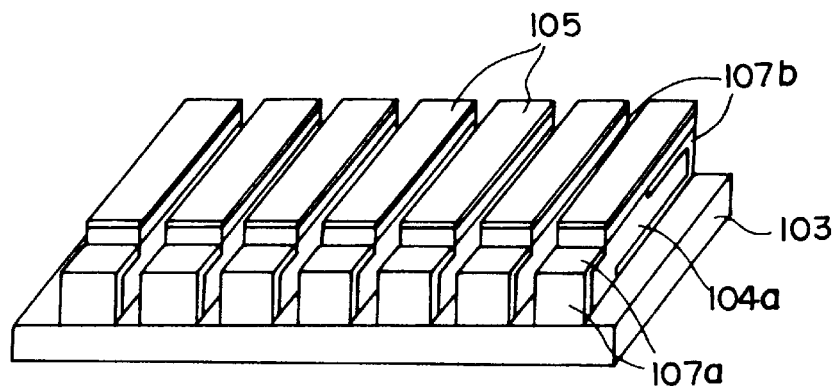
FIG. 34 is a perspective view showing the manufacturing procedures of the ultrasonic probe device according to the seventh embodiment of the present invention in which the ultrasonic transducer is divided into transducer elements.

Subsequently, the substantially rectangular flexible backing member 103 having a predetermined thickness is adhered (joined) to the back surface of the ultrasonic transducer plate 104 using a heat reaction type film-shaped adhesive, as shown in FIG. 33. Joining of the backing material 103 may be conducted prior to joining of the acoustic matching layers 105. Thereafter, as shown in FIG. 34, the ultrasonic transducer plate 104 is cut from the front surface side thereof on which the acoustic matching layers 105A and 105B are formed along the slice direction at a predetermined pitch and in a predetermined depth using a dies. The cutting pitch of the dies is set according to a desired pitch of the transducer elements. The cutting depth of the dies is adequately set with the thickness of the backing member 103 taken into consideration.

As the result of the cutting, the plurality of fine transducer elements 104a are formed in an array on the backing member 103. The plurality of arrayed transducer elements 104a constitute the group of transducer elements. The backing member 103 may be joined to a backing member constituting a reinforcing layer or a backing member holder (which is thin and flexible layer), as in the case of the first embodiment.

Figure 35:
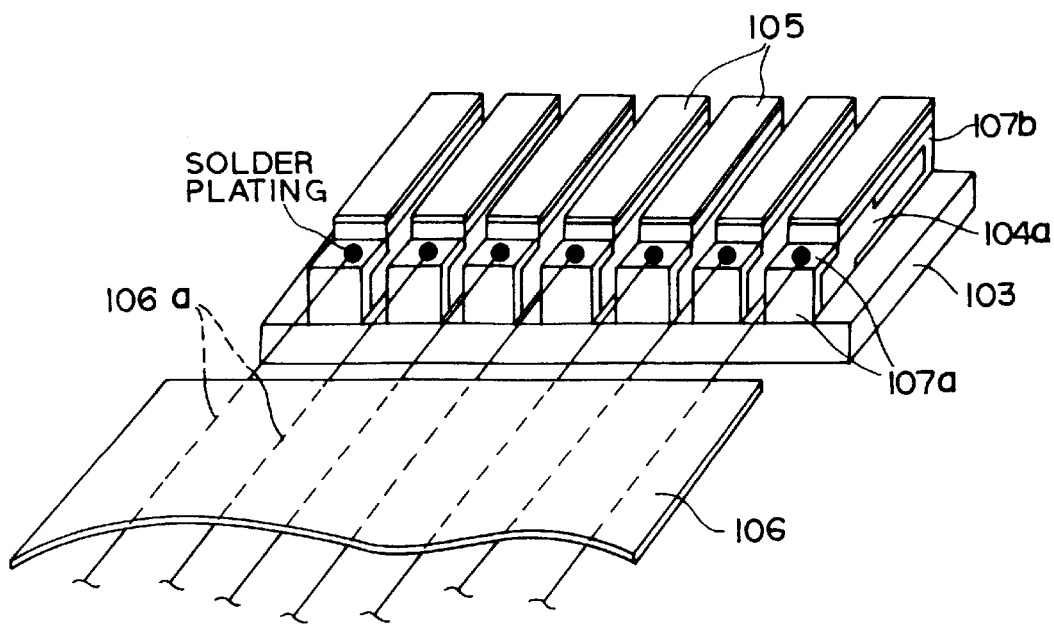
FIG. 35 is a perspective view showing the manufacturing procedures of the ultrasonic probe device according to the seventh embodiment of the present invention in which a flexible printed circuit is joined to the ultrasonic transducer.

Next, the sheet-shaped FPC 106 having the exposed pattern 106a at the distal end thereof, shown in FIG. 35, is prepared. The pattern pitch of the exposed pattern corresponds to the predetermined pitch of the transducer elements 104a. The exposed pattern 106a of the FPC 106 is joined to the electrode layers 107a formed on the front surfaces of the transducer elements 104a by, for example, the resistance welding method by parallel gap (see FIG. 12) or the pulse heat heating method (see FIG. 13) for connecting signal lines.

The ultrasonic transducer 104 arranged in the manner described above is curved along the direction in which the transducer elements 104a are arrayed, and adhered to the outer peripheral surface of the container 102 (see FIGS. 30 and 31). Accordingly, the FPC 106 body is wound around the outer peripheral surface of the container 102. Thereafter, the sheet- and ring-shaped grounding plate 108 made of, for example, copper is adhered to the grounding electrode layers 107b formed on the lateral other side surfaces of each of the transducer elements 104a by, for example, soldering, as shown in FIG. 30. A grounding line 108a is connected to the grounding plate 108. The grounding line 108a is passed through a hollow portion of the container 102 and extended to a rear stage for grounding.

A filler (not shown), such as silicon adhesive, is filled in the gap between the adjacent transducer elements as an insulating resin material. Thereafter, the acoustic lens 109 is adhered to the outer peripheral surfaces of the respective transducer elements 104a to constitute the ultrasonic probe 101. The ultrasonic probe 101 is incorporated in a probe (casing) to constitute the probe head 100. The other end portion of the FPC 106 is connected to the transmitting/receiving circuit via a connector and a cable which are not shown, whereby manufacture of the ultrasonic probe device is almost completed.

In this embodiment, after the ultrasonic transducer 104 has been divided into the transducer elements 104a, the exposed pattern 106a of the FPC 106 is joined to the electrode layers 107a formed on the front surfaces of the transducer elements 104a. Further, the grounding plate 108 is joined to the grounding electrode layers 107b formed on the other lateral side surfaces of the respective transducer elements 104a after the exposed pattern 106a of the FPC 106 has been connected to the ultrasonic transducer 104 and the ultrasonic transducer plate 104 has been curved.

In other words, since the ultrasonic transducer plate 104 is divided into the large number of transducer elements 104a before the FPC 106 and the grounding plate 108 are not yet joined thereto, effective and smooth division can be performed, and a problem involving electrode peel-off can be eliminated. In addition to these advantages, since no resistance to division caused by the hardness of the FPC 106 and grounding plate 108 exists, element peel-off is eliminated. Further, since no resistance to curving of the ultrasonic transducer 104 exists, the ultrasonic transducer plate can be curved freely, enabling a radial type ultrasonic probe device having a very small curvature to be manufactured.

Furthermore, the seventh embodiment is constructed such that the FPC 106 is joined to the electrode layers 107a formed on the front surfaces of the transducer elements 104a and such that the grounding plate 108 is joined to the electrode layers 107b formed on the other lateral side surfaces of the transducer elements 104a. That is, since connection of the signal lines or the grounding lines is not performed on the back surfaces of the transducer elements 104a, the back surface of the ultrasonic transducer 104 can be adhered directly to the backing member 103. Accordingly, adhesion between the transducer 104 and the backing member 103 can be increased, thus increasing manufacture yield.

As mentioned above, it is possible according to the seventh embodiment of the present invention to manufacture electronic radial scanning type ultrasonic probe devices for body cavity having a very small curvature on an industrial basis while maintaining yield at a high value. The seventh embodiment has the following advantages as compared with a conventional mechanical radial scanning type ultrasonic probe device.

(1) Since multi-stage focusing during transmission and dynamic variable aperture and focus during reception are possible, bearing resolution is improved, thus improving image quality.

(2) Color Doppler is enabled, enabling blood flow diagnosis.

(3) A degree of freedom of scanning is greatly increased, thus enabling displays of various combinations of B mode, M mode and Doppler mode.

(4) Since the ultrasonic probe device is hollow, it can be combined with a front viewing type optical endoscope, thus enabling various diagnosis.

Figure 36:
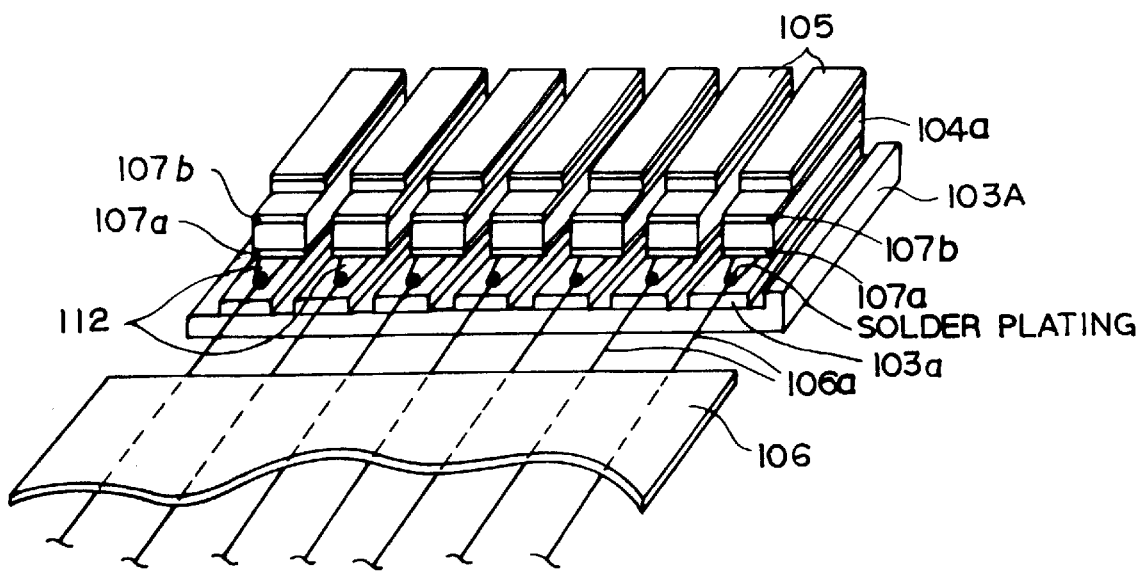
FIG. 36 is a perspective view showing the manufacturing procedures of the ultrasonic probe device according to an eighth embodiment of the present invention in which an FPC is joined to lands formed on a backing member.
Figure 37:
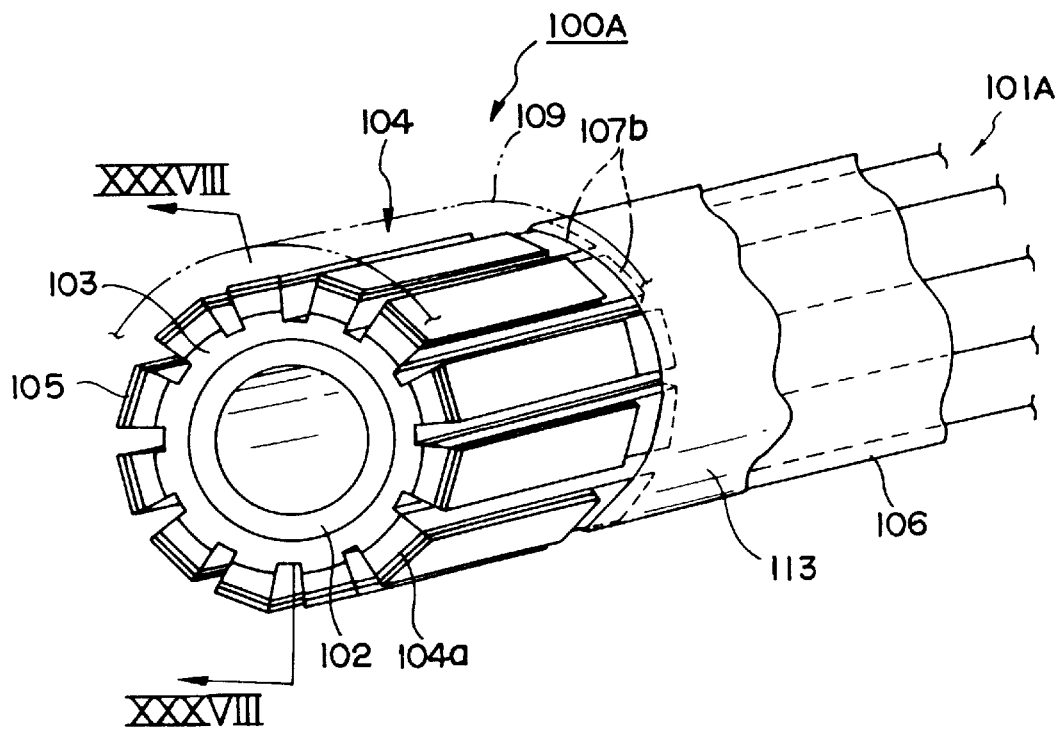
FIG. 37 is a perspective view showing the manufacturing procedures and structure of the ultrasonic probe device according to the eighth embodiment of the present invention in which the ultrasonic transducer is curved and wound around a container.

An eighth embodiment of the present invention will now be described with reference to FIGS. 36 to 38. Identical reference numerals in these figures to those in the seventh embodiment represent similar to identical elements, description thereof being omitted.

To manufacture the ultrasonic probe device according to the eighth embodiment of the present invention, a substantially rectangular flexible backing member 103A having a predetermined thickness is prepared. The backing member 103A has a conductive pattern 103a formed on the upper surface (front surface) thereof at a preset pitch. The backing member 103A also has a land 112, serving as a signal line connecting portion, formed on the upper surface thereof at a predetermined position including the conductive pattern 103a.

Next, a substantially rectangular piezoelectric plate 104B made of a ceramic material, such as lead titanate zirconate porcelain, is prepared. The short side of the piezoelectric plate 104B is shorter than the short side of the backing member 103A. The piezoelectric element 104B has the electrode layer 107a for signal lines formed beforehand on the back surface thereof. The piezoelectric element 104B also has the electrode layer 107b for grounding formed beforehand on the front surface thereof. The piezoelectric plate 104B with the electrode layers 107a and 107b formed thereon constitutes an ultrasonic transducer 104.

The front surface of the backing member 103A and the back surface of the transducer 104 are joined to each other using, for example, a heat reaction type film-shaped adhesive. Accordingly, the conductive pattern 103a formed on the front surface of the backing member 103A is electrically connected to the electrode layer 107a formed on the back surface of the transducer 104. At that time, the lateral front end portion of the backing member 103A, which is along a longitudinal dirrection is exposed, as shown in FIG. 36.

Next, cutting is performed on the transducer 104 from the front surface of the transducer 104 along the conductive pattern 103a formed on the front surface of the backing member 103A at a predetermined pitch at a predetermined cutting depth, as in the case of the seventh embodiment. Accordingly, the plurality of fine transducer elements 104a are formed in an array on the backing member 103A. The plurality of arrayed transducer elements 104a constitute the group of transducer elements.

The conductive pattern and exposed pattern 106a of the FPC 106 are formed on the FPC 106 beforehand at a pitch corresponding to the pitch at which the conductive pattern 103a is formed on the backing material 103A.

As shown in FIG. 35, the exposed pattern 106a of the FPC 106 is joined to the conductive pattern 103a exposed at the front end portion of the backing member 103A through the lands 112 by soldering which utilizes either the resistance welding method by parallel gap (see FIG. 12) or the pulse heat heating method (see FIG. 13). Accordingly, the FPC 106 is connected to the signal electrode layers 107a of the transducer elements 104a through the conductive pattern 103a of the backing member 103A to achieve signal electrode connection.

The ultrasonic transducer 104 arranged in the manner described above is curved along the direction in which the transducer elements 104a are arrayed, and adhered to the outer peripheral surface of the container 102. As a result, the FPC 106 body is wound around the outer peripheral surface of the container 102.

Thereafter, a substantially rectangular sheet-shaped grounding plate 113 made of, for example, copper is prepared. Substantially, the grounding plate 113 is wound around the container 112 in such a manner that the end portion of the long side thereof is superimposed on end portions of the electrode layers 107b formed on the front surface of the transducer elements 104a which are close to the apparatus, as shown in FIGS. 37 and 38. Joining of the superimposed portion is performed by soldering or using a conductive adhesive.

A filler (not shown), such as silicon adhesive, is filled in the gap between the adjacent transducer elements as an insulating resin material. Thereafter, the acoustic lens 109 is adhered to the outer peripheral surfaces of the respective transducer elements 104a to constitute the ultrasonic probe 101A. The ultrasonic probe 101A is incorporated in a probe (casing) to constitute the probe head 100A. The other end portion of the FPC 106 is connected to the transmitting/receiving circuit via a connector and a cable which are not shown, whereby manufacture of the ultrasonic probe device is almost completed.

In this embodiment, since the conductive pattern 103a and the land 112, serving as the signal line connecting portion, are formed on the front surface of the backing member 103A at a predetermined pitch and at a predetermined position including the conductive pattern 103a, respectively, and since the FPC 106, which is an conductor, is joined to the land 112 for connection of signal lines, connection of signal lines is further facilitated. The other functions and effects of the eighth embodiment are the same as those of the seventh embodiment.

It is not necessary for the conductive pattern 103a formed on the backing member 103A to be one which is separated beforehand for each element. Separation of the conductive pattern 103a may be electrically performed by a dies at the time of division of the ultrasonic transducer 104.

In the seventh and eighth embodiments, after the ultrasonic transducer 104 is divided into the transducer elements 104a, the exposed pattern 106a of the FPC 106 is joined to the electrode layers (the seventh embodiment) on the front surfaces of the transducer elements 104a or to the conductive pattern 103a (the eighth embodiment) on the backing member 103A by, for instance, pulse heat soldering. After the joining, the transducer 104 is curved and adhered to the cylindrical surface of the container 102. However, the manufacturing procedures of the present invention are not limited to the above-described procedures. That is, after the ultrasonic transducer 104 has been divided into the transducer elements 104a, curving and adhesion of the ultrasonic transducer 104 to the cylindrical surface of the container 102 may be performed first which are followed by joining of the exposed pattern 106a of the FPC 106 to the electrode layers 107a on the front surfaces of the transducer elements 104a (the seventh embodiment) or to the conductive pattern 103a on the backing member 103A (the eighth embodiment) by either the resistance welding method or the pulse heat heating method.

Figure 38:
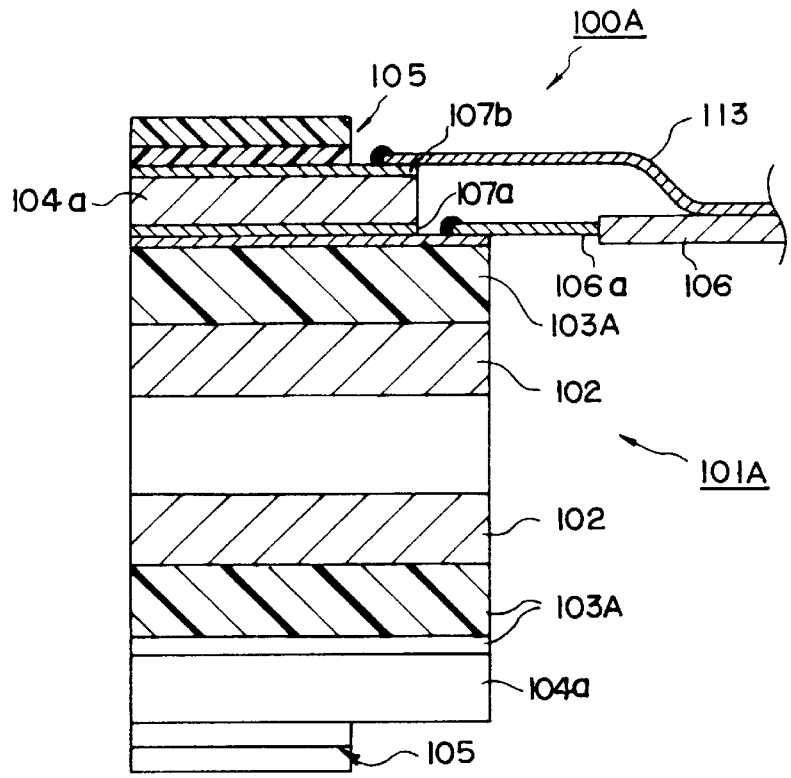
FIG. 38 is a cross-section taken along the line XXXVIII—XXXVIII of FIG. 37.
Figure 39:
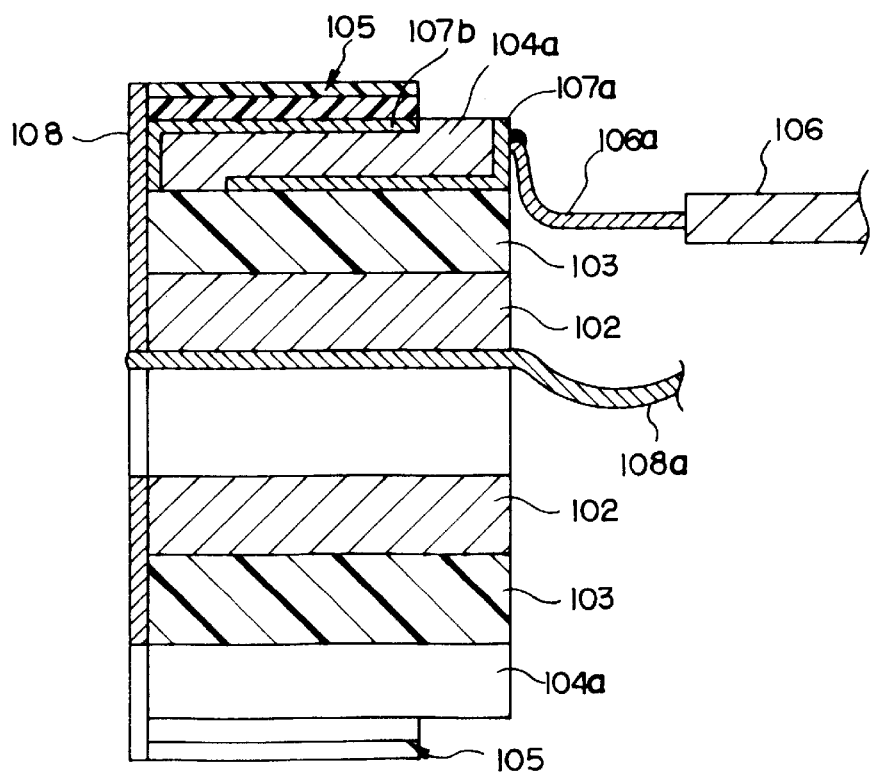
FIG. 39 is a cross-sectional view showing joining of the FPC to the electrode layer formed on the side surface of the transducer element.
Figure 40:
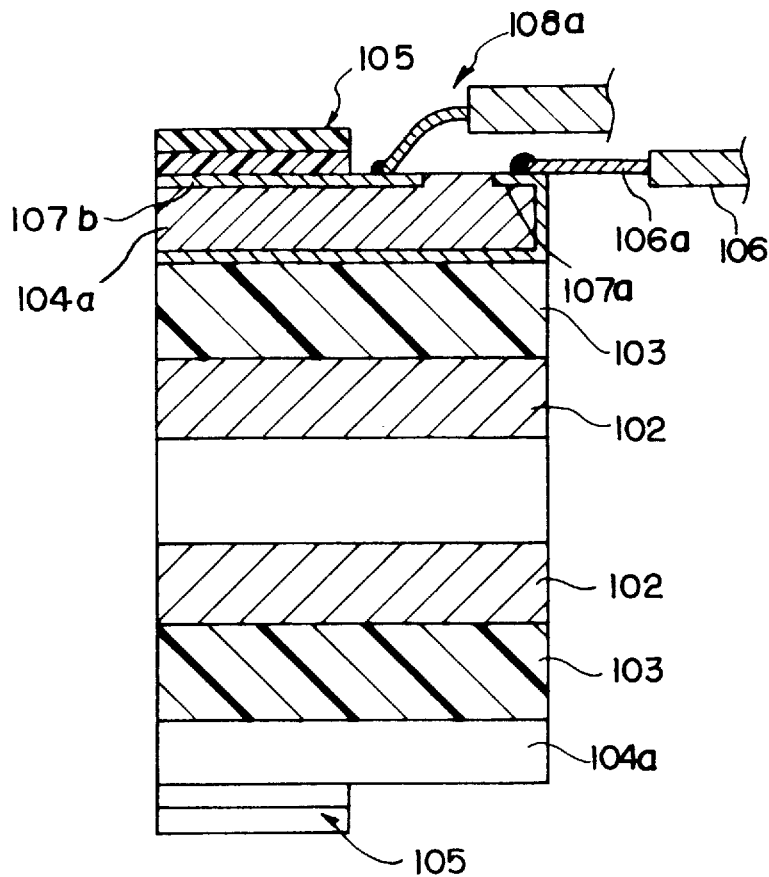
FIG. 40 is a cross-sectional view showing joining of the grounding line to the electrode layer formed on the front surface of the transducer element.

While the seventh embodiment has been constructed such that the electrode layers 107a for signal lines are formed on the front surfaces of the transducer elements 104a and such that the exposed pattern 106a of the FPC 106 is joined to the electrode layers 107a for signal line connection, modifications thereof might include a probe device constructed such that electrode layers 107a for signal lines are formed on one lateral side surfaces of the transducer elements 104a and on the back surfaces thereof, and such that the exposed pattern 106a of the FPC 106 is joined to the portion of the electrode layers 107a formed on the one side surfaces of the transducer elements 104a for signal line connection, as shown in FIG. 38. Further, while the seventh embodiment has been constructed such that the grounding plate 108 is joined to the electrode layers 107b formed on one lateral side surfaces of the transducer elements 104a for connecting grounding lines, modifications might contain a probe device in which the grounding electrode layers 107b are formed on the front surfaces of the transducer elements 104a and in which grounding lines 108a are connected directly to the electrode layers 107b, as shown in FIG. 40.

Figure 41:
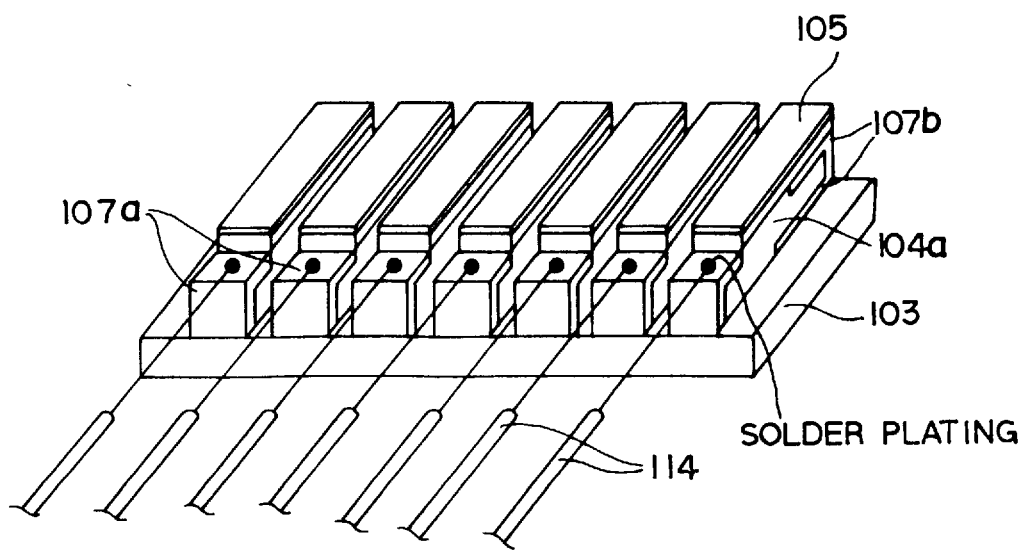
FIG. 41 is a perspective view showing joining of coaxial cables to the electrode layers formed on the front surfaces of the transducer elements.
Figure 42:
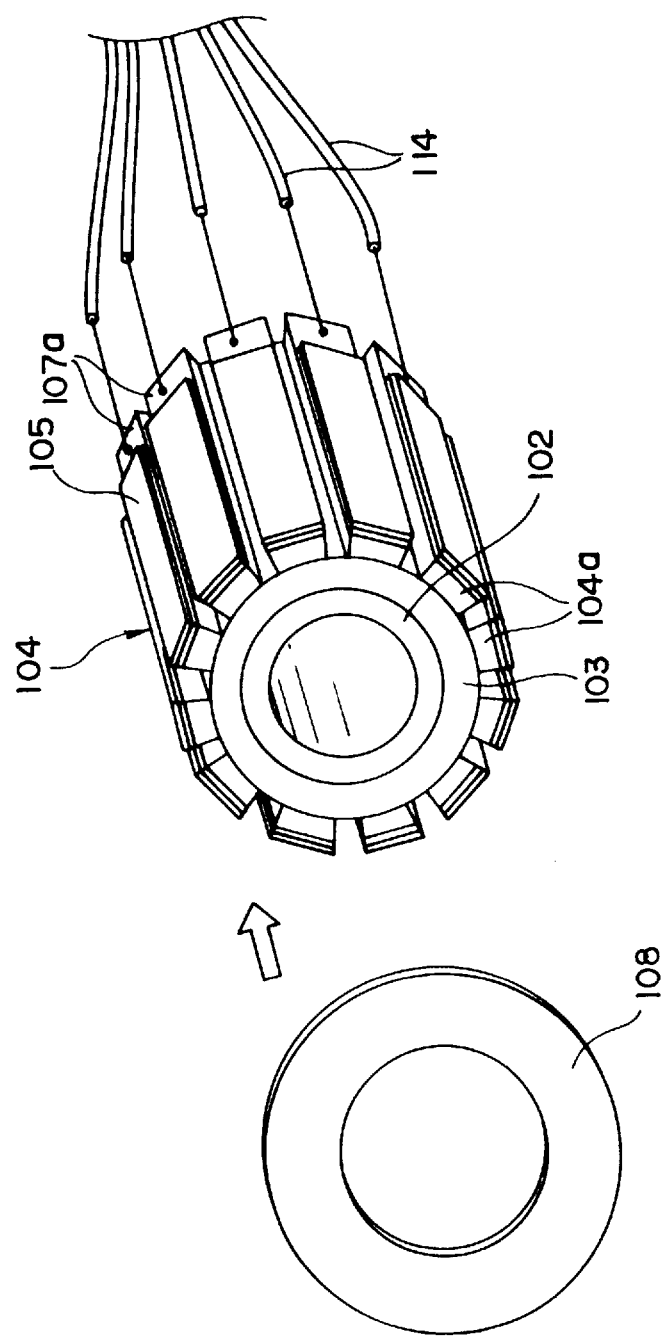
FIG. 42 is a perspective view showing a schematic structure of the ultrasonic probe device with the coaxial cables joined thereto.
Figure 43:
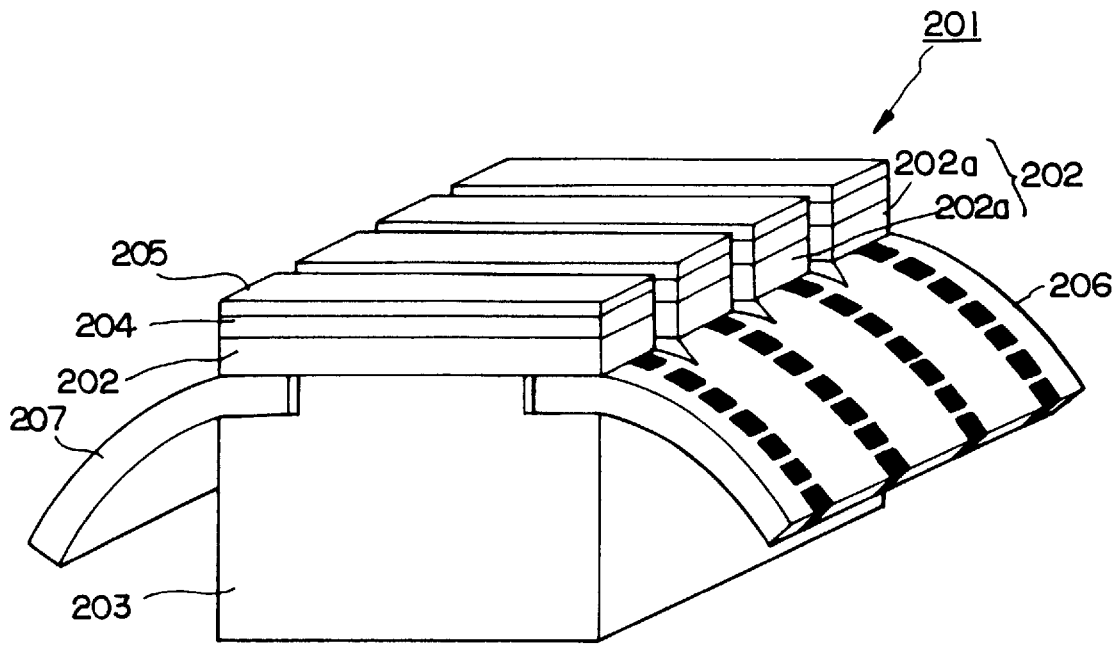
FIG. 43 is a perspective view of a probe head of a conventional ultrasonic probe device.
Figure 44:
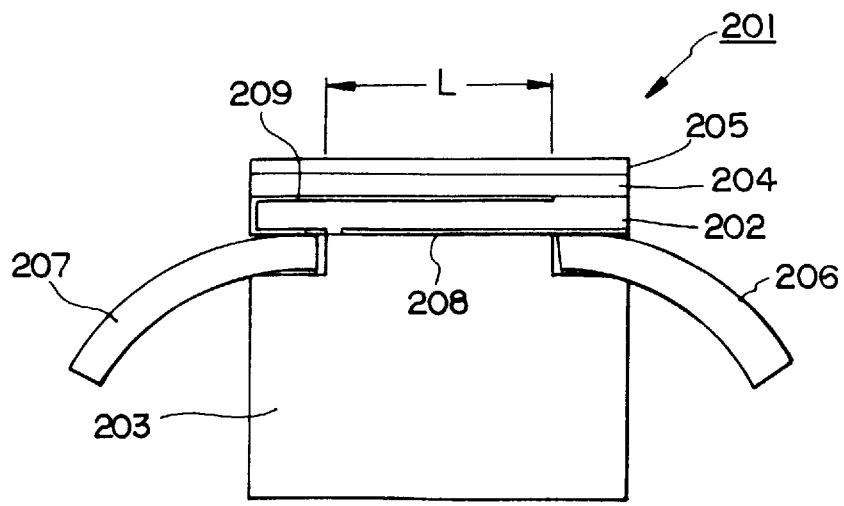
FIG. 44 is a side elevational view of the probe head shown in FIG. 43.

Furthermore, while the seventh and eighth embodiments have been described as employing the FPC 106 whose distal end is exposed as a conductor, modifications might contemplate a probe device which employs coaxial cables 114 in place of the FPC 106 for signal line connection, as shown in FIGS. 41 and 42. That is, the electrode layer 107a formed on one lateral side surface of each of the transducer elements 104a is joined to the signal line of each of the coaxial cables 114 by, for instance, soldering for electrode connection. Where the coaxial cables 114 are employed, grounding electrode connection may be performed by adequately binding grounding lines (outer skins) of the coaxial cables 114 and by joining the grounding lines to the grounding electrode.

When compared with normally employed cables, the coaxial cables 114 have low transmission loss and low crosstalk. Thus, in addition to the above-described effects, the use of the coaxial cables enables manufacture of an ultrasonic probe device exhibiting low crosstalk and low disturbance noise.

Furthermore, although the method of manufacturing a radial type ultrasonic probe device has been described in the seventh and eighth embodiments, it can also be applied to the manufacture of a convex type ultrasonic probe device which employs a arc-shaped container in place of the cylindrical container.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. An ultrasonic probe having a plurality of ultrasonic transducer elements, arranged in a row along a plane, each having an outer surface consisting of a front surface for transmitting and receiving an ultrasonic signal, a back surface opposite to the front surface, and first and second opposing side surfaces connecting between the front surface and the back surface, and wherein each of the plurality of ultrasonic transducer elements is driven by a driving electric signal so as to transmit and receive the ultrasonic signal, the ultrasonic probe comprising:

a plurality of pair of electrodes each formed on at least one of the first and second side surfaces of the plurality of ultrasonic transducer elements; and a pair of conductors having a plurality of pair of joint portions joined to the pair of electrodes, respectively, each of the joint portions of the pair of conductors being positioned on at least one of the first and second side surfaces of the plurality of ultrasonic transducer elements.

2. The ultrasonic probe according to claim 1, wherein said respective ones of the paired-electrodes of the respective ultrasonic transducer elements are formed on the respective first side surfaces of the respective ultrasonic transducer elements through an interposing layer and respective others of the paired electrodes thereof are formed on the respective second side surfaces thereof through the interposing layer, said interposing layer being composed of at least one component selected from Cr, Ni, Ti, and Sn.

3. The ultrasonic probe according to claim 1, wherein each of said paired electrodes of each of the ultrasonic transducer elements has joint parts joined to the joint portions of the paired conductors, respectively, each of said joint parts of the paired electrodes being made of at least one of Au, Ag, and Cu.

4. The ultrasonic probe according to claim 1, wherein each of said paired electrodes of each of the ultrasonic transducer elements has joint parts joined to the joint portions of the paired conductors, respectively, each of said joint parts of the paired electrodes being formed by at least one of deposition, sputtering, baking, or plating.

5. The ultrasonic probe according to claim 1, wherein each of said paired electrodes of each of the ultrasonic transducer elements has joint parts joined to the joint portions of the paired conductors, respectively, each of said joint parts of the paired electrodes being an Ag baked electrode.

6. The ultrasonic probe according to claim 1, wherein said respective ones of paired electrodes of the respective ultrasonic transducer elements are substantially opposite to the respective others of paired electrodes thereof and are electrically disconnected to the respective others of paired electrodes thereof.

7. The ultrasonic probe according to claim 6, wherein said one of paired conductors includes a signal conductor for transmitting the driving electric signal to the respective ones of the paired electrodes of the respective ultrasonic transducer elements through the joint portions of the one of paired conductors and said other of paired conductors includes a ground conductor for grounding the respective others of the paired electrodes thereof through the joint portions of the other of paired conductors.

8. The ultrasonic probe according to claim 7, wherein said signal conductor is a flexible printed circuit having a plurality of signal lines respective one end of which are exposed, said exposed ends of the signal lines including the joint portions of the one of paired conductors, respectively, and said ground conductor is a grounding plate having one end portion thereof, said one end portion of the grounding plate including the joint portions of the other of paired conductors.

9. The ultrasonic probe according to claim 8, wherein said respective joint portions of the exposed ends of the signal lines axe positioned on the respective first side surfaces of the respective ultrasonic transducer elements and said respective joint portions of the one end portion of the grounding plate are positioned on the respective second side surfaces thereof.

10. The ultrasonic probe according to claim 9, wherein said respective joint portions of the exposed ends of the signal lines are joined to the respective ones of the paired electrodes formed on the respective first side surfaces of the respective ultrasonic transducer elements by microsoldering and said respective joint portions of the one and portion of the grounding plate are joined to the respective others of the paired electrodes formed on the respective second side surfaces of the respective ultrasonic transducer elements by soldering or a conductive adhesive.

11. The ultrasonic probe according to claim 10, wherein said respective joint portions of the exposed ends of the signal lines joined to the respective ones of the paired electrodes formed thereon are solder plated to a thickness of 3 $\mu$m to 20 $\mu$m.

12. The ultrasonic probe according to claim 11, wherein when said respective joint portions of the exposed ends of the signal lines are provided so as to be contact with the respective ones of the paired electrodes, a welding machine having a welding chip constituting parallel gap which is in contact with the respective joint portions of the exposed ends generates heat from the respective joint portions of the exposed ends by making current flow through the welding chip and the respective joint portions of the exposed ends thereby reflowing the respective solder plates of the respective joint portions so that the respective joint portions are soldered to the respective ones of the paired electrodes and then are joined to the respective ones of the paired electrodes.

13. The ultrasonic probe according to claim 11, wherein when said respective joint portions of the exposed ends of the signal lines are provided so as to be contact with the respective ones of the paired electrodes, a pulse heating device having a welding chip which is in contact with the respective joint portions of the exposed ends provides heat generated by a resistance of the heating chip by making current flow through the heating chip for the respective joint portions of the exposed ends thereby reflowing the respective solder plates of the respective joint portions thereof so that the respective joint portions thereof are soldered to the respective ones of the paired electrodes and then are joined to the respective ones of the paired electrodes.

14. The ultrasonic probe according to claim 10, wherein said respective joint portions of the one end portion of the grounding plate joined to the respective others of the paired electrodes formed thereon are solder plated to a thickness of 3 μm to 20 μm.

15. The ultrasonic probe according to claim 10, wherein at least two joint portions of the exposed ends of the signal lines are united by soldering for linking at least two ultrasonic transducer elements adjoining each other, said at least two ultrasonic transducer elements being joined to the at least two joint portions thereof.

16. The ultrasonic probe according to claim 10, wherein each of said joint portions of the exposed ends of the signal lines runs in a direction, the direction crossing normal directions of each of the ultrasonic transducer elements.

17. The ultrasonic probe according to claim 10, wherein said exposed pattern side of the flexible printed circuit is divided into a plurality of portions.

18. The ultrasonic probe according to claim 8, wherein said respective joint portions of the exposed ends of the signal lines are positioned at the respective first side surfaces of the respective ultrasonic transducer elements and said respective joint portions of the one end portion of the grounding plate are positioned on one end portion of the respective front surfaces thereof.

19. The ultrasonic probe according to claim 8, wherein said respective joint portions of the exposed ends of the signal lines are positioned on one end portions of the respective front surfaces of the respective ultrasonic transducer elements and said respective joint portions of the one end portion of the grounding plate are positioned on the respective second side surfaces thereof.

20. The ultrasonic probe according to claim 8, wherein said respective joint portions of the exposed ends of the signal lines are positioned on one end portions of the respective front surfaces of the respective ultrasonic transducer elements and said respective joint portions of the one end portion of the grounding plate are positioned on other and portion of the respective front surfaces thereof.

21. The ultrasonic probe according to claim 1, wherein each of the paired conductors comprises a coaxial cable.

22. The ultrasonic probe according to claim 1, wherein one of the paired conductors comprises a coaxial cable and the other of the paired conductors thereof comprises a grounding plate.

23. An ultrasonic probe device having an ultrasonic probe incorporated in a probe head of the ultrasonic probe device, in which the ultrasonic probe has a plurality of ultrasonic transducer elements, arranged in a row along a plane, each having an outer surface consisting of a front surface for transmitting and receiving an ultrasonic signal, a back surface opposite to the front surface, and first and second opposing side surfaces connecting between the front surface and the back surface, and wherein each of the plurality of ultrasonic transducer elements is driven by a driving electric signal so as to transmit and receive the ultrasonic signal, the probe device comprising:

an acoustic matching layer formed on the front surface of each of the plurality of ultrasonic transducer elements;

a backing member provided on the back surface of each of the plurality of ultrasonic transducer elements;

an acoustic lens provided so as to cover the acoustic matching layer;

a plurality of pair of electrodes each formed on at least one of the first and second side surfaces of each of the ultrasonic transducer elements; and a pair of conductors having a plurality of pair of joint portions joined to the pair of electrodes, respectively, each of said joint portions of the pair of conductors being positioned on at least one of the first and second side surfaces of each of the ultrasonic transducer elements.

* * * * *